US009833145B2

(12) United States Patent
Jeong et al.

(10) Patent No.: US 9,833,145 B2
(45) Date of Patent: Dec. 5, 2017

(54) METHOD FOR SIMULTANEOUSLY DETECTING FLUORESCENCE AND RAMAN SIGNALS FOR MULTIPLE FLUORESCENCE AND RAMAN SIGNAL TARGETS, AND MEDICAL IMAGING DEVICE FOR SIMULTANEOUSLY DETECTING MULTIPLE TARGETS USING THE METHOD

(71) Applicant: SNU R&DB FOUNDATION, Seoul (KR)

(72) Inventors: Dae Hong Jeong, Seoul (KR); Keon Wook Kang, Seoul (KR); Dong Soo Lee, Seoul (KR); Yoon Sik Lee, Anyang-si (KR); Gun Sung Kim, Anyang-si (KR); Bong Hyun Jun, Daegu (KR); Jin Chul Paeng, Seoul (KR); Ho Young Lee, Seoul (KR); Yun Sang Lee, Seoul (KR)

(73) Assignee: SNU R&DB FOUNDATION, Seoul (KR)

( * ) Notice: Subject to any disclaimer, the term of this patent is extended or adjusted under 35 U.S.C. 154(b) by 0 days.

(21) Appl. No.: 15/398,038

(22) Filed: Jan. 4, 2017

(65) Prior Publication Data

US 2017/0112380 A1  Apr. 27, 2017

Related U.S. Application Data

(63) Continuation-in-part of application No. 13/816,035, filed as application No. PCT/KR2011/005915 on Aug. 11, 2011, now abandoned.

(30) Foreign Application Priority Data

Aug. 11, 2010 (KR) .................. 10-2010-0077565

(51) Int. Cl.
*A61B 5/00* (2006.01)
*A61K 49/00* (2006.01)
(Continued)

(52) U.S. Cl.
CPC ........ *A61B 5/0071* (2013.01); *A61B 1/00009* (2013.01); *A61B 1/015* (2013.01);
(Continued)

(58) Field of Classification Search
CPC ..... A61B 5/0071; A61B 5/0075; A61B 1/015; A61B 1/063; A61B 1/00009; A61B 1/043;
(Continued)

(56) References Cited

U.S. PATENT DOCUMENTS 7,230,958 B2   6/2007  Chang et al.
7,285,089 B2   10/2007 Viellerobe et al.
(Continued)

FOREIGN PATENT DOCUMENTS

JP   2002136469   5/2002
JP   2009511175   3/2009
(Continued)

OTHER PUBLICATIONS

Gioux, et al., Improved optical sub-systems for intraoperative near-infrared flourescence imaging, Proc. of SPIE, vol. 6009, 2005.
(Continued)

*Primary Examiner* — Long V Le
*Assistant Examiner* — Angela M Hoffa
(74) *Attorney, Agent, or Firm* — Cantor Colburn LLP

(57) ABSTRACT

Provided are a method for simultaneously detecting fluorescence and Raman signals for multiple fluorescence and Raman signal targets, and a medical imaging device for simultaneously detecting multiple targets using the method. The method includes: injecting at least one marker particle
(Continued)

comprising Raman markers and receptors into the body of an animal, which can be a human; irradiating a laser beam onto the body of the animal; and detecting the optical signals emitted by the marker particle after the irradiation of the laser beam separately as fluorescence signals and Raman signals. The simultaneous detection of multiple targets may be performed even without scanning optical signals emitted by the marker particle individually with different optical fibers. As an examination may be performed by injecting surface-enhanced Raman marker particles, weak Raman signals may be augmented so as to obtain a more accurate diagnosis result in real time.

14 Claims, 18 Drawing Sheets

(51) Int. Cl.
| | | |
|---|---|---|
| *A61B 90/00* | (2016.01) | |
| *A61M 11/00* | (2006.01) | |
| *A61B 1/06* | (2006.01) | |
| *A61B 1/015* | (2006.01) | |
| *A61B 1/04* | (2006.01) | |
| *A61B 1/00* | (2006.01) | |
| *B82Y 5/00* | (2011.01) | |

(52) U.S. Cl.
CPC .............. *A61B 1/043* (2013.01); *A61B 1/063* (2013.01); *A61B 5/0035* (2013.01); *A61B 5/0075* (2013.01); *A61B 5/0084* (2013.01); *A61K 49/00* (2013.01); *A61K 49/0002* (2013.01); *A61K 49/0093* (2013.01); *A61M 11/00* (2013.01); *A61B 5/0068* (2013.01); *A61B 2090/397* (2016.02); *A61B 2090/3933* (2016.02); *A61B 2090/3941* (2016.02); *A61B 2090/3995* (2016.02); *A61B 2562/0285* (2013.01); *A61B 2562/046* (2013.01); *A61M 2205/0244* (2013.01); *B82Y 5/00* (2013.01)

(58) Field of Classification Search
CPC ................ A61B 5/0084; A61B 5/0035; A61B 2562/046; A61B 2562/0285; A61K 49/0002; A61K 49/0093; A61K 49/00; A61M 11/00
See application file for complete search history.

(56) References Cited

U.S. PATENT DOCUMENTS

| | | | |
|---|---|---|---|
| 7,336,990 B2 | 2/2008 | Genet et al. | |
| 7,359,040 B1 | 4/2008 | Pendell-Jones et al. | |
| 7,383,077 B2 | 6/2008 | Zeng | |
| 7,436,501 B2 | 10/2008 | Hashimoto et al. | |
| 7,447,539 B2 | 11/2008 | Genet et al. | |
| 7,525,653 B1 | 4/2009 | Hug et al. | |
| 7,720,526 B1 | 5/2010 | Modell | |
| 7,928,408 B2* | 4/2011 | Ok | G01J 3/02 250/458.1 |
| 7,982,870 B2 | 7/2011 | Lee et al. | |
| 8,018,582 B2 | 9/2011 | Jeong et al. | |
| 8,064,064 B2 | 11/2011 | Kim et al. | |
| 8,385,615 B2 | 2/2013 | Levenson et al. | |
| 8,634,607 B2 | 1/2014 | Levenson et al. | |
| 2005/0130163 A1 | 6/2005 | Smith et al. | |
| 2005/0240107 A1 | 10/2005 | Alfano et al. | |
| 2006/0173355 A1 | 8/2006 | Alfano et al. | |
| 2006/0238745 A1 | 10/2006 | Hashimoto et al. | |
| 2007/0002435 A1 | 1/2007 | Ye et al. | |
| 2007/0167836 A1 | 7/2007 | Scepanovic et al. | |
| 2007/0167838 A1 | 7/2007 | Hubble et al. | |
| 2008/0007716 A1 | 1/2008 | Makoto | |
| 2008/0051645 A1 | 2/2008 | Mihailo et al. | |
| 2009/0023999 A1 | 1/2009 | Mathieu et al. | |
| 2010/0020312 A1 | 1/2010 | Jeong et al. | |
| 2010/0072067 A1 | 3/2010 | Lee et al. | |
| 2010/0129261 A1 | 5/2010 | Kim et al. | |
| 2010/0321683 A1 | 12/2010 | Lee et al. | |
| 2011/0152692 A1 | 6/2011 | Nie et al. | |
| 2011/0160577 A1 | 6/2011 | Kaji et al. | |
| 2013/0137944 A1* | 5/2013 | Jeong | A61B 1/015 600/317 |
| 2014/0199235 A1 | 7/2014 | Jeong et al. | |

FOREIGN PATENT DOCUMENTS

| | | |
|---|---|---|
| JP | 2010060698 | 3/2010 |
| KR | 1020050034199 | 4/2005 |
| KR | 1020070014964 | 2/2007 |
| KR | 1020080111950 | 12/2008 |
| KR | 100892629 | 4/2009 |
| KR | 1020090092512 | 9/2009 |
| KR | 1020100004458 | 1/2010 |
| WO | 2007125300 | 11/2007 |
| WO | 2008001978 | 1/2008 |

OTHER PUBLICATIONS

International Search Report—PCT/KR2011/005915 dated May 1, 2012.
Keren, et al., Noninvasive molecular imaging of small living subjects using Raman spectroscopy, PNAS, vol. 105, No. 15, Apr. 15, 2008, pp. 5844-5849.
Mohs, et al., Hand-held Spectroscopic Device for In Vivo and Intraoperative Tumor Detection: Contrast Enhancement, Detection Sensitivity, and Tissue Penetration, Anal. Chem., 2010, 82, pp. 9058-9065.
Su, et al., Composite Organic-Inorganic Nanoparticles (COINs) with Chemically Encoded Optical Signatures, Nano letters, vol. 5, No. 1, 2005, pp. 49-54.
Sun, et al., Composite Organic-Inorganic Nanoparticles as Raman Labels for Tissue Analysis, Nano letters, vol. 7, No. 2, 2007, pp. 351-356.

* cited by examiner

△ Natural sponge

METHOD FOR SIMULTANEOUSLY DETECTING FLUORESCENCE AND RAMAN SIGNALS FOR MULTIPLE FLUORESCENCE AND RAMAN SIGNAL TARGETS, AND MEDICAL IMAGING DEVICE FOR SIMULTANEOUSLY DETECTING MULTIPLE TARGETS USING THE METHOD

CROSS-REFERENCE TO RELATED APPLICATION

This application is a Continuation-in-part of application Ser. No. 13/816,035, filed Feb. 8, 2013, which is a national entry of PCT Application No. PCT/KR11/005915 filed on Aug. 11, 2011, which claims priority to and the benefit of Korean Patent Application No. 10-2010-0077565, filed on Aug. 11, 2010, the entire contents of which are incorporated herein by reference.

TECHNICAL FIELD

The present disclosure relates to a method associated with medical imaging, i.e., to a method for obtaining image information on multiple targets by simultaneously detecting fluorescence and Raman signals and a medical imaging device thereof, and more particularly, to a medical imaging device including, for example, an endoscopic device, an optical fiber probe, or long distance optical system employing an optical fiber bundle probe for use in the in-vivo diagnosis of a disease of an animal including human, and a signal detection method using the same for utilization for a method for diagnosing in-vivo diseases.

BACKGROUND

In modern medical science, in-vivo disease diagnosis is conducted using a variety of imaging equipments such as MRI, PET, CT or endoscopy, each of which having different scope of applications and advantages and disadvantages according to features thereof.

A medical imaging equipment proposed herein is similar to currently-available endoscope in terms of the fact that the equipment is capable of acquiring two-dimensional image of a specific site inside a human body or a site exposed to outside, using a probe for insertion into the human body or a long distance optical system having a long-working distance, while also providing real time-based qualitative analysis of multiple markers using marker nanoparticles binding thereto and signals. However, the proposed imaging equipment according to the present disclosure provides wider and more efficient range of applications than endoscopes. The advantages are obtained from a technology that simultaneously introduces multi signal components such as fluorescence and Raman signals (to be specific, SERS signals) for marker nanoparticles, along with an optical system which is capable of measuring the same with efficiency.

Endoscope non-invasively examines in-vivo the interior of organs such as digestive system or respiratory system. Diagnosis method using the endoscope is photodynamic diagnosis. Taking cancer diagnosis for example, invasive biopsy extracts biological sample and culture cancer tissue. However, optical biopsy using endoscopy does not require extraction of biological sample, but examines a suspected site by irradiating light. This method thus saves pains on the patient's side, and also offers convenience and simple process on the side of a practitioner who can use images. Additionally, endoscope offers advantages such as accurate cancer diagnosis and early detection of cancer.

Conventional endoscopic examination involves observation on mucous membrane using white light, using natural color representation of minute color shifting of mucous membrane to provide detection of minimal disease change which is as small as several millimeters. Meanwhile, the endoscopic investigation utilizing white light has insufficient ability to recognize dysplasia generally occurring in Barrett esophagus or to detect or diagnose colorectal polyp from non-tumor. Accordingly, biopsy and histopathologic examination are separately required, to characterize positivity of a sample or malignancy. However, biopsy has drawbacks mentioned above, and other shortcomings that it is prone to sampling error, or increased cost and lengthening time of inspection due to need for histopathologic examination.

Indeed, the white light-based endoscopic examination is considered to be a relatively simple screen technology, and it is not considered to be as technological as implied by the term 'endoscopic imaging' which generally refers to those technologies that illuminate artificial lights in-vivo to living organism and construct an image based on extraction/processing/interpretation of optical information that can be acquired from the living organism.

To compensate for the above-mentioned drawbacks, fluorescent imaging technology was proposed as the endoscopic imaging technology that utilizes fluorescence, according to which presence or absence of a targeted material can be analyzed with increased accuracy and in real time by distinguishing differences of colors or the like released from normal and abnormal structures with a diagnostic equipment, using autofluorescence which is naturally emitted from biological structure in response to a predetermined frequency of laser light emitted thereto, or photosensitizer or biomarker selectively remaining on a cancerous structure. The fluorescent imaging technology thus enabled in-vivo analysis of presence of targeted material on living organism, with increased accuracy and in a real-time basis (U.S. Pat. No. 7,285,089 et al.)

Fluorescence is used in a wide range of areas as a marker substance due to its high sensitivity that can detect even a single molecule. A considerable number of imaging technologies on marker materials have been proposed so far, including the in-vivo fluorescence imaging technology on marker material as proposed by Gambir et al. However, the fluorescence imaging technology has fundamental limitation particularly in terms of simultaneous detection on multiple biomarkers due to relatively wider bandwidth of the fluorescent spectra.

Accordingly, newer optical diagnostic technologies such as light scattering spectroscopy, or optical coherence tomography have been suggested so far, and attempts were continuously made to examine the states of the structures in details. The Raman spectrometry is gaining attention, as its way of detecting vibration spectra of molecules gives availability in a variety of optical fields and also it contains information about the structure of molecules. Since the Raman spectrometry basically enables characterization of biological constituents such as proteins or DNA based on the differences of molecular structures thereof. The Raman spectrometry is thus considered to be effective in the detection and diagnosis as to, for example, whether the polyp generated on mucous membrane is tumor or nontumor.

Raman scattering based on vibration of molecules has optical characteristics which are distinguished from the energy of incident light. Accordingly, Raman scattering has narrow line width, and different scattering wavelengths depending on the types and vibrations of the scattered molecules. Further, the Raman marker materials that express Raman scattering do not show photobleaching characteristic like fluorescence. By utilizing the above-mentioned optical characteristics, it will be possible to encode a plurality of biomarkers distinctively within a narrow optical region, and it is thus possible to detect signals from multiple biomarkers by single diagnosis performance and to perform diagnosis on molecular structure-based sample using the Raman spectrometry.

Many studies are currently conducted on the imaging analysis equipment which utilizes Raman spectrometry. By way of example, JP Patent Application Publication No. 2002-136469 (Reference 1) discloses an endoscopic apparatus employing a Raman spectrometer and an optical fiber, and JP Patent Application Publication No. 2009-511175 (Reference 2) discloses an imaging apparatus which achieves microimages using CARS signal.

However, many improvements are necessary to achieve accurate diagnosis by the Raman spectrometry utilizing endoscopy, because the Raman signal emitted from the sample itself is very weak, and most Raman signals are interfered with autofluorescence of the sample, thus causing difficulty of discriminating Raman spectra of normal site from those of abnormal site. That is, due to basically weak signal strength, the Raman signals are not easily detected due to various noises or fluorescence.

US Patent Application Publication No. 2008-0007716 (Reference 3) attempts to solve the problem of Raman signals being interfered with autofluorescence of a sample, by providing a method for removing fluorescent interference with a Shifted Excitation Raman Difference Spectroscopy (SERDS) system, but is not efficient enough to overcome the basic characteristic of the Raman signals, i.e., weakness of the signals. Further, most Raman spectrometry-based technologies suggested so far have not solved inconvenience of having to record spectra by scanning with individual optical fibers included in the optical fiber bundle and conduct imaging with respect to a specific band. Therefore, notwithstanding the advantageously narrow line width of Raman signals, practical utilization thereof for the simultaneous detection of multiple markers has limits.

SUMMARY

The present disclosure has been proposed to overcome the problems occurring in the prior art, and an object of the present disclosure is to provide a method for simultaneously detecting fluorescence and Raman signals for multiple targets of various diseases including cancer of an incision of an animal including human in a procedure such as surgery, and to a medical imaging device for simultaneously detecting multiple targets using the method.

The present disclosure has been proposed to overcome the problems mentioned above, a method for simultaneously detecting fluorescence and Raman signals for multiple targets in one embodiment may include steps of: injecting marker particles and one or more marker particles including Raman marker particle and receptor into a body of an animal including human; illuminating a laser light into the body of the animal; and detecting, by separating an optical signal emitted after the illuminating into a fluorescent signal and a Raman signal.

The above steps inject, and thus binds marker nanoparticles, which are surface-treated to bind to targeting sites (target such as a disease or the like including specific cancer cells), separating multi-signals emitted from the bound marker nanoparticles and thereby determines location and type of the target.

The injecting may use various methods such as oral administration or injection by needle, but not limited thereto. Additional steps may be included, such as, directly spraying the marker particle onto a test structure inside the body of the animal using a spraying means connected to a probe of the medical imaging device, or injecting the marker particle through blood vessels.

Further, it may help to determine the relative location of the marker particle by determining form and location of a test structure using Rayleigh scattering and autofluorescence from cells and tissues, in addition to the fluorescence by the marker particle.

The detecting step may include steps of filtering, and thus removing laser light from the emitted optical signal, dividing a path of the filtered optical signal into a first and a second paths, and detecting a fluorescence signal from the optical signal of the first divided path and detecting a Raman signal from the optical signal of the second path, whereby the test structure can be imaged with the fluorescence signal (i.e., autofluorescence naturally emitted from the sample itself) and analyzed with the Raman signal.

The marker particle according to one embodiment of the present disclosure may additionally include a fluorescence dye, in which case the location of the test structure can be easily determined based on the fluorescence signal emitted from the fluorescence dye and analyzed with the Raman signal. That is, if the fluorescence signal is naturally emitted from the sample itself, two-dimensional imaging using general fluorescence may be conducted, while if the fluorescence signal is originated from the fluorescence dye included in the marker particle, this is used in the determination of the location of the test structure. Further, after the detecting step, the step of analyzing the test structure using the Raman signal is subsequently performed.

The marker particle for use in the medical imaging device and detecting method according to the present disclosure may preferably use a surface-enhanced Raman marker particle incorporating therein so-called illuminating component, which may include the Raman reporter molecules adsorbed on metal nano particle including at least one of silver (Ag), gold (Au) or copper (Cu), and fluorescence materials including dyes or quantum dots co-added with core-shell structure nanoparticle including the same.

The probe particle may be so structured that the structure thereof may additionally include silica shell surrounding the fluorescence dye, the Raman reporter molecules and the metal nanoparticle or may be surface-treated to enhance other biocompatibility.

Further, the marker particle may include silica core particle to further increase quality of SERS signal, in which the silica core particle may additionally include magnetic nanoparticles to further expand the functionality of the marker particle.

That is, the present disclosure necessarily involves use of probe nanoparticles generating strong Raman signal (particularly, SERS signals), which are attached to the targeted site to investigate presence or absence of various targets and types of the targets based on the characteristic Raman signal thereof, and preferably and additionally generating fluorescence providing additional effects such as easy location tracing of targets due to simultaneous emission of fluorescence signal and the Raman signal.

The most basic form of the marker particle has to emit enhanced Raman signal, which may be provided in a core-shell form including a silica core incorporating therein a metal nanoparticle including at least one of gold (Au), silver (Ag) or copper (Cu), Raman marker material adhered onto the metal nano particle and a shell protecting the same (Korean Patent No. 10-0733085, Korean Patent Application Publication No. 10-2008-0111950). Another example can also be found in COIN (Nano Letters, 2007, 7(2), 351-356) which discloses use of metal nano particle and bundle thereof as the core, and metal and hollow shell.

In any case, using silica shell may protect the Raman marker material within nanoparticles, increase biocompatibility of the nanoparticle, and facilitate introduction of receptors for the binding to respective targets. The receptor may use a marker material-specific receptor including any one selected from a group consisting of enzyme substrate, ligand, amino acid, peptide, protein, nucleic acid, lipid, co-factor, carbohydrate or antibody.

Among implementations of the multi signals, a technology to use both fluorescence and Raman signal is particularly advantageous for the imaging and multi detection. A F-SERs Dot (Korean Patent Application Publication No. 10-2008-0111950) as one embodiment of the present disclosure relates to additionally including fluorescence dye to the shell in the process of forming the shell of the marker particle. In addition to the above implementation, other examples are also possible. For example, the fluorescence dye may be included in the core as a dye-doped silica, and the fluorescence dye itself may be various fluorescence signal emitting material other than general organic dye, such as quantum dot. As explained above, the fluorescence signal emitted from the fluorescence dye may be advantageously used to determine the location of a test structure, while the Raman signal is used to perform analysis on the same. In this process, fluorescence signal may be naturally emitted from the test structure itself (i.e., autofluorescence), and this may be used to perform two-dimensional imaging of the test structure with the above-mentioned optical equipment. If the signal is originated from the fluorescence dye included in the marker particle, this may advantageously used for determining the location of the test structure.

To ensure that the simultaneous detection of multi signals is performed efficiently, the fluorescence dye is so selected as to be placed in the longer wavelength domain than the Raman signal to avoid overlapping with the Raman signal. The doubling of the target number of the simultaneous detection is enabled because different targets can be distinguished with the fluorescence signal before the discrimination by the Raman signal. If (n) fluorescence dyes are introduced with respect to (m) Raman signal marker particles, nano marker for simultaneously detecting (m×n) multiple targets is possible. However, too many fluorescence markers are less preferred, considering the wide bandwidth of fluorescence. Accordingly, if a plurality of fluorescence markers are necessary, two to four fluorescence markers may be sufficient.

The present disclosure has been made to overcome the problems mentioned above, and in one embodiment, provides a medical imaging device for simultaneously detecting multiple fluorescence and Raman signal targets which may include a light source which emits a laser light, an image guide which guides the laser light emitted from the light source and optical signals of an incident light emitted from a test structure or from marker particles which comprise a Raman marker material to emit Raman signals and receptors and which are bound to the test structure, a light collector which is connected to the image guide and which collects the optical signals, a scanner which is connected to the image guide and which scans the optical signals of the incident light, a light separator comprising a beam splitter connected to the scanner to separate a path of the incident light into a first path and a second path so that the lights are emitted separately, a fluorescence signal detector which detects fluorescence signals from the optical signals of the first path separated at the light separator, and a Raman signal detector which detects Raman scattering lights from the optical signals of the second path separated at the light separator to construct a Raman spectrum.

The light collector may be implemented in various forms for broader use of the optical equipment according to the present disclosure, and it is preferable to use optical fiber bundle or remote distance optical system. Since the optical fiber bundle has long length and small diameter, it is possible to directly contact this to the exposed site of the incision in the process of surgery, or when implemented in the form of slant tip, it is also possible to penetrate the same into skin for observation. Further, the optical fiber bundle may be connected to the endoscope to allow easier observation of a targeted site inside the living body. Further, while the end of the optical fiber bundle can be exposed as is, it is possible to acquire minute confocal images in the cell level, if microoptical system such as ball lens or GRIN lens, etc., is attached and used. The long-working distance lens may be used as the remote distance optical system, and this is particularly advantageous in observing the exposed target site in a contactless manner.

The light separator may additionally include an edge filter which is placed between the scanner, the fluorescence signal detector and the Raman signal detector, to removes, by filtering, the laser light from the optical signals incoming from the scanner.

It is necessary that the light separator additionally includes the edge filter to remove, by filtering, Rayleigh scattering light which corresponds to the wavelength of the laser light which is relatively stronger among the optical signals incoming from the scanner. It is also necessary to include a filter and a beam splitter to separate the optical signals into Raman signals and fluorescence signals and guide these to paths 1 and 2, to ensure that the fluorescence and Raman signals are collected efficiently. The Rayleigh removal filter may be implemented with various specifications and in various arrangements.

Further, the image guide and the light collector may additionally include a spray means to spray the marker particles onto the test structure, in which the spray means may additionally include a washing means to wash the test structure.

According to an aspect of the present disclosure, there is provided a method for simultaneously detecting, by a medical imaging device, fluorescence signals and Raman signals for multiple targets in a test structure inside a body of an animal. The method may comprise a step of directly spraying a plurality of marker particles onto the test structure. In this method, each marker particle may be adapted to simultaneously generate fluorescence signals in a first wavelength range and Raman signals in a second wavelength range and include one or more Raman marker particles, receptors, one or more fluorescence dyes and one or more metallic nanoparticles may comprise at least one of silver (Ag), gold (Au) or copper (Cu). Further, the first and second wavelength ranges being separate from one another without mutual interference. In addition, the method may comprise steps of emitting a laser light onto the test structure inside the body of the animal so that one or more of the marker particles sprayed onto the test structure emit optical signals comprising the fluorescence signals and the Raman signals; collecting, by an optical fiber bundle of the medical imaging device, the optical signals emitted from the one or more of the marker particles sprayed onto the test structure; separating the optical signals into a first optical path containing the fluorescence signals in the first wavelength range and a second optical path containing the Raman signals in the second wavelength range; and simultaneously detecting the fluorescence signals in the first optical path for constructing a fluorescence image and the Raman signals in the second optical path for constructing a SERS (Surface Enhanced Raman Scattering) spectrum. In this method, the fluorescence image may be indicative of locations of the multiple targets in the test structure based on the detected fluorescence signals, and the SERS spectrum may be indicative of types of the multiple targets in the test structure based on the detected Raman signals.

According to another aspect of the present disclosure, there is provided a medical imaging device for simultaneously detecting fluorescence signals and Raman signals for a plurality of targets in a test structure inside a body of an animal. The medical imaging device may comprise a plurality of marker particles. In this device, each marker particle may be adapted to simultaneously generate fluorescence signals in a first wavelength range and Raman signals in a second wavelength range and include one or more Raman marker particles, one or more receptors, one or more fluorescence dyes and one or more metallic nanoparticles comprising at least one of silver (Ag), gold (Au) or copper (Cu). Further, the first and second wavelength ranges are separate from one another without mutual interference. In addition, the medical imaging device may comprise a spray device adapted to spray the plurality of marker particles onto the test structure; a probe including an optical fiber bundle configured to guide a laser light onto the test structure and collect optical signals comprising the fluorescence signals and the Raman signals emitted from one or more of the marker particles sprayed onto the test structure in response to the laser light; a scanner connected to the probe and adapted to scan the optical signals comprising the fluorescence signals and the Raman signals; a light separator comprising a beam splitter connected to the scanner to separate a path of the optical signals into a first path including the fluorescence signals in the first wavelength range and a second path including the Raman signals in the second wavelength range; a fluorescence signal detector configured to detect the fluorescence signals from in the first path for constructing a fluorescence image; and a Raman signal detector configured to detect the Raman signals in the second path for constructing a SERS spectrum. In this device, the fluorescence image may be indicative of locations of the multiple targets in the test structure based on the detected fluorescence signals, and the SERS spectrum may be indicative of types of the multiple targets in the test structure based on the detected Raman signals.

According to another aspect of the present disclosure, there is provided a medical imaging device for simultaneously detecting fluorescence signals and Raman signals for a plurality of targets in a test structure inside a body of an animal. The medical imaging device may comprise a storage tank containing a plurality of marker particles. In this device, each marker particle may be adapted to simultaneously generate fluorescence signals in a first wavelength range and Raman signals in a second wavelength range. The first and second wavelength ranges may be separate from one another without mutual interference. In addition, the medical imaging device may comprise a spray device adapted to spray the plurality of marker particles from the storage tank onto the test structure; a probe including an optical fiber bundle configured to guide a laser light onto the test structure and simultaneously collect optical signals comprising the fluorescence signals and the Raman signals emitted from one or more of the marker particles sprayed onto the test structure in response to the laser light, the optical fiber bundle comprising a plurality of optical fibers, each optical fiber configured to collect one of the optical signals indicative of a pixel among a plurality of pixels defining an image of the test structure; a scanner connected to the probe and adapted to confocally scan the collected optical signals received from the optical fiber bundle; a light separator connected to the scanner to separate a path of the scanned optical signals into a first path including the fluorescence signals in the first wavelength range and a second path including the Raman signals in the second wavelength range; a fluorescence signal detector configured to detect the fluorescence signals in the first path, wherein the detected fluorescence signals are indicative of pixels associated with the plurality of targets to which the sprayed marker particles are attached; a Raman signal detector configured to detect the Raman signals in the second path and construct a SERS spectrum indicative of at least one property of the plurality of targets in the test structure based on the detected Raman signals; and an image processor configured to construct the image of the test structure indicative of locations of the plurality of targets in the test structure based on at least the detected fluorescence signals in the scanned optical signals.

According to another aspect of the present disclosure, there is provided a medical imaging device for simultaneously detecting fluorescence signals and Raman signals for a plurality of targets in a test structure inside a body of an animal. The medical imaging device may comprise a storage tank containing a plurality of marker particles. In this device, each marker particle may be adapted to simultaneously generate one or more fluorescence signals in a first wavelength range and one or more Raman signals in a second wavelength range. The first and second wavelength ranges may be separate from one another without mutual interference. In addition, the medical imaging device may comprise a spray device adapted to spray the plurality of marker particles from the storage tank onto the test structure; a first and a second light source configured to generate a first and a second laser light, respectively; a probe configured to guide the laser lights from the first and the second light sources onto the test structure and collect optical signals comprising the fluorescence signals and the Raman signals emitted from one or more of the marker particles sprayed onto the test structure in response to the laser lights; a light separator configured to separate a path of the optical signals from the probe into a first path including the fluorescence signals in the first wavelength range and a second path including the Raman signals in the second wavelength range; a fluorescence signal detector configured to detect the fluorescence signals in the first path for constructing a fluorescence image indicative of locations of the plurality of targets in the test structure based on the detected fluorescence signals; and a Raman signal detector configured to detect the Raman signals in the second path for constructing a SERS (Surface Enhanced Raman Scattering) spectrum indicative of at least one property of the plurality of targets in the test structure based on the detected Raman signals.

According to the present disclosure, it is possible to easily perform simultaneous detection of multiple targets using multiple optical signals emitted from a test structure.

Further, according to the present disclosure, since the Raman marker particles with fluorescence components incorporated thereto are injected into a living body with a spray device or the like, more accurate diagnostic results based on multiple biomarker analysis can be obtained in a real-time basis.

DETAILED DESCRIPTION

The present disclosure will be explained in greater detail below with reference to exemplary embodiments.

Figure 1:
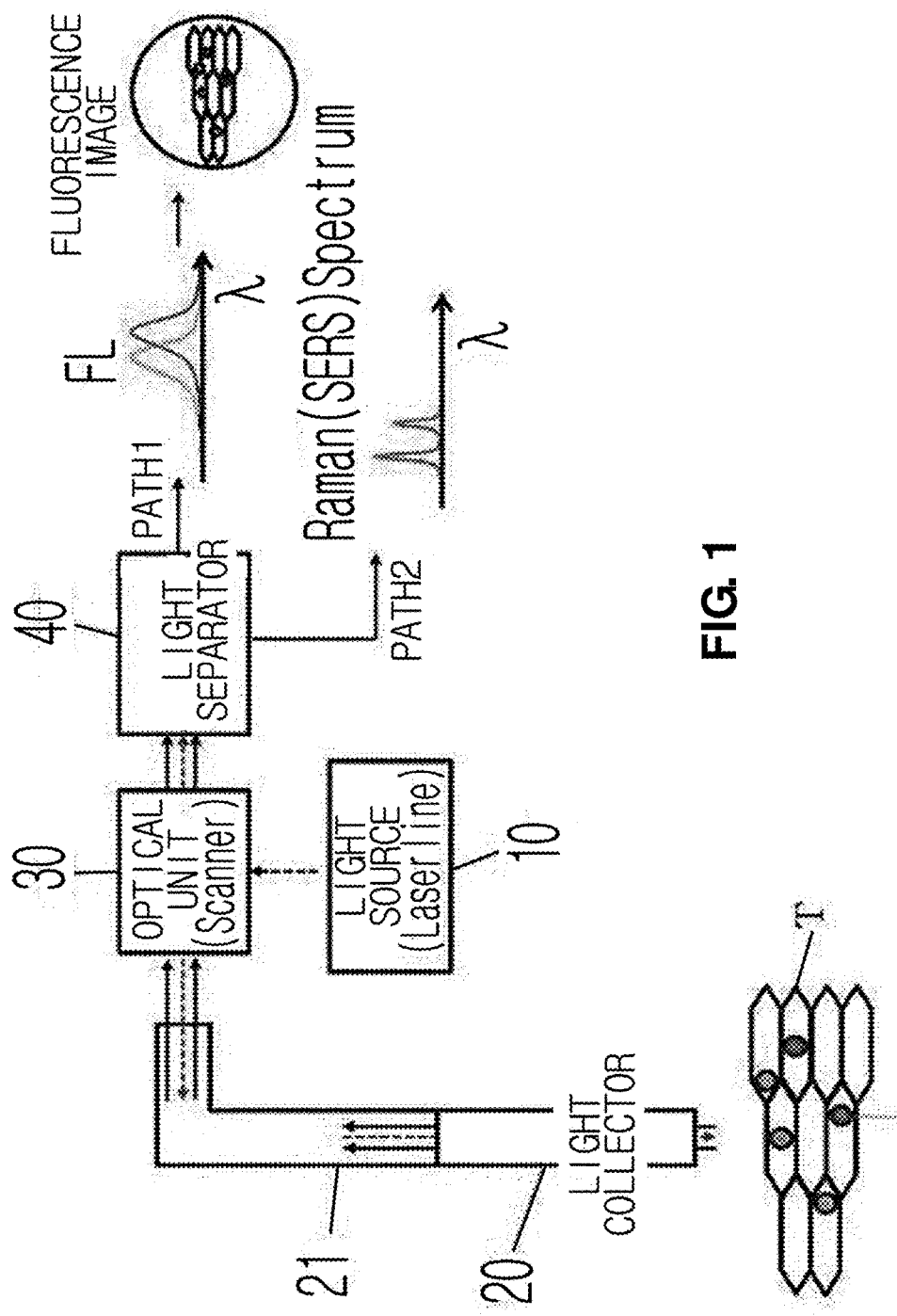
FIG. 1 is a schematic view illustrating a structure and operation of a medical imaging device for simultaneously detecting multiple fluorescence and Raman signal targets according to the present disclosure.

FIG. 1 is an overall, schematic view illustrating a structure and operation of a medical imaging device for simultaneously detecting multiple fluorescence and Raman signal targets according to the present disclosure.

Referring to FIG. 1, the medical imaging device according to the present disclosure includes a light source 10, an image guide 21 including a bundle of optical fibers, a light collector 20, a scanner 30, and a light separator 40, according to which accurate diagnosis is performed as a path of the optical signal collected at the light collector 20 and passed through the optical fiber bundle 12 and the scanner 30 is divided into a path 1 and a path 2, a location of a target material (T) (e.g., area the marker particle is bound to targeting cell and tissue) is confirmed, and a type and a relative amount of marked particle by the various Raman signals separated to path 2.

For an optical system that provides two dimensional imaging and mobility, a technically well-developed and also well-known optical fiber bundle system 21 including scanner 30 is used, and marker nanoparticle (e.g., F-SERS dot, etc.), which uses both fluorescence signal having technical superiority in terms of real-time imaging and Raman scattering signal having superiority for multiple detection, is used, and fluorescence imaging and Raman spectra are acquired for the signal detection by separating the fluorescence signal and the Raman signal. Since the marker particle is bio-conjugated to recognize biological molecule to diagnose, the targeted marker particle emits fluorescence and Raman signals so that the optical signal delivered to the optical fiber bundle passes through the optical system and separated into fluorescence imaging and Raman spectrum for measure thereof. The measured fluorescence image indicates the targeted location among the cells and tissues in a living organism, and the Raman spectrum indicates the type of the targeted biological molecule. To be specific, since the Raman spectrum has bandwidth below approximately 10 cm-1, it is possible to use numerous different signals from the visible ray area, from excitation energy and narrow spectrometry area below 2000 cm-1, to fabricate various types of marker nanoparticles including Raman marker materials that emit Raman signals at different locations, and also possible to simultaneously detect multiple targeted biological molecules using such marker nanoparticles. The Raman scattering signals used herein utilize the surface enhanced Raman scattering (SERS) effect, and silver, gold and nano structures of various forms can be utilized to acquire enhanced Raman scattering signals.

The optical signals of marker nanoparticles are constructed with fluorescence signals which do not overlap with the SERS signals by the molecules adhered to silver and gold surfaces. Since SERS signals can select various adsorbate molecules, numerous different signals can be incorporated, and although the identical fluorescence signals can be selected, relatively distinguishing signals may be incorporated within an optically distinguishable range, in which case various types of signals can be implemented based on combinations of SERS signals and fluorescence signals, and various immunoassay strategies can be provided. By way of example, using the fluorescence signals emitted from the fluorescence dye, it is possible to advantageously determine the location of the test structure, and using the Raman signals, it is possible to analyze the same. That is, if the fluorescence signal is naturally emitted from the sample itself, two dimensional imaging using general fluorescence can be implemented, while if the fluorescence signal is originated from the fluorescence dye included in the marker particles, this can be used in the determination of a location of the test structure.

Figure 2:
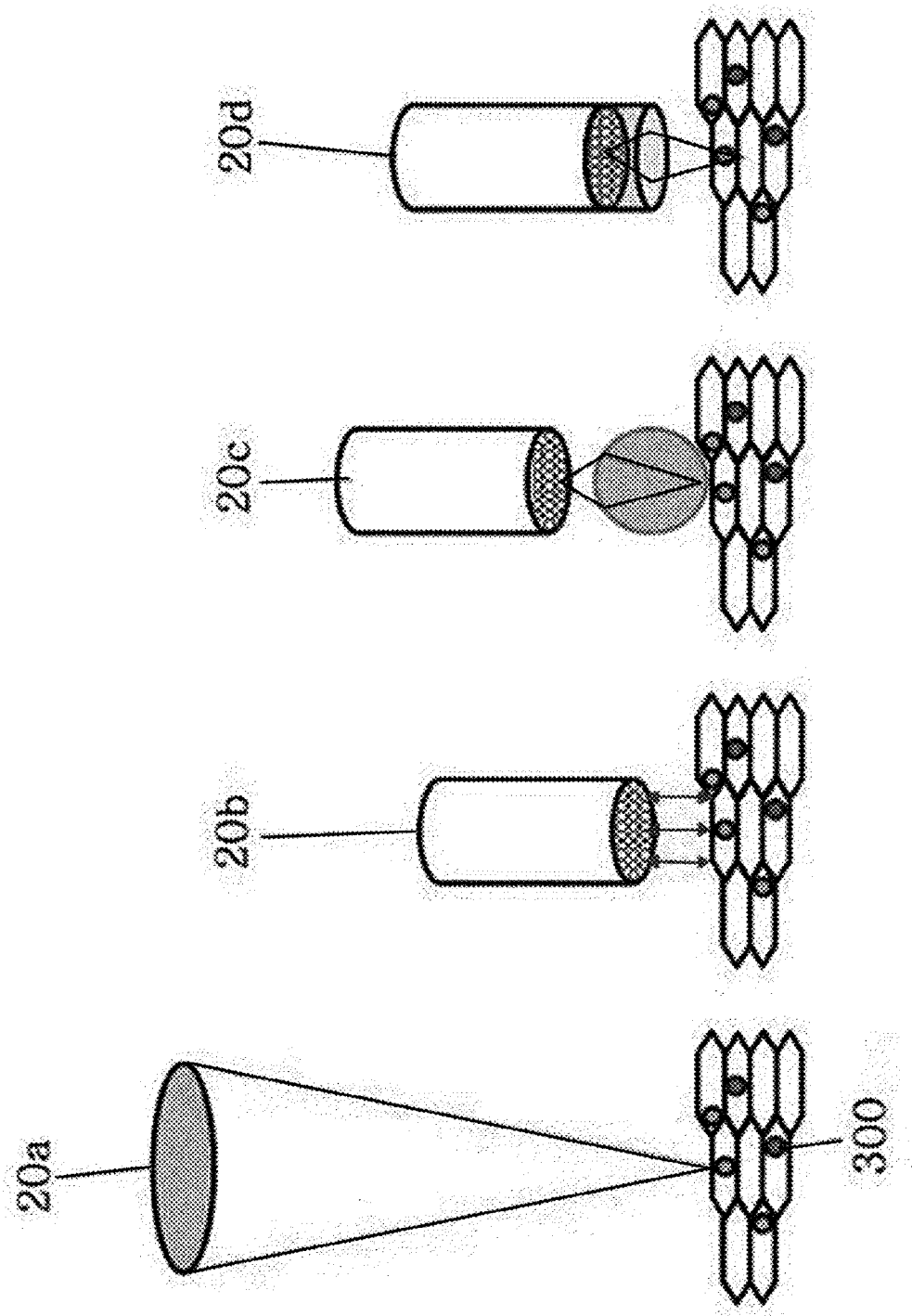
FIG. 2 schematically illustrates a structure of a light collector of a medical imaging device for simultaneously detecting multiple fluorescence and Raman signal targets according to the present disclosure.

FIG. 2 schematically illustrates a structure of a light collector of a medical imaging device for simultaneously detecting multiple fluorescence and Raman signal targets according to the present disclosure. In one example, it is possible to use a lens system (reference numeral '20a') such as so-called 'long-working distance lens', which is used at a several centimeter working distance (e.g., intraoperative imaging equipment (FLARE: Fluorescence-assisted resection and exploration, Proc. SPIE, Vol. 6009, 60090C (2005)) at a terminal end of the optical fiber bundle optical system 21, according to which one is able to perform imaging and multi measure during a surgery; or use micro optics such as GRIN lens 20d and Ball lens 20c, or use the optical fiber bundle as a probe (i.e., without employing any lens at all) according to which one is able to perform imaging and multi measure by measuring near-distance sample which is at a micrometer working distance (U.S. Pat. No. 7,336,990 B2, US 2009/0023999 A1)

The optical fiber bundle probe 20b, 20c, and/or 20d may particularly be used in combination with endoscope. The guide of the endoscope may additionally include a spraying means which sprays the marker particles onto the test structure, to thus simultaneously detect the fluorescence and Raman signals in real-time basis in vivo and thus provide improved accuracy of the diagnosis. Meanwhile, additional functions of the medical imaging diagnosis may be incorporated by combining the functions of the conventional nuclear medical imaging equipment such as MRI or PET, in which case the nuclear medical imaging equipment may detect the disease region, while the optical fiber bundle probe may measure the corresponding region to construct multiple diagnostic image.

Figure 3:
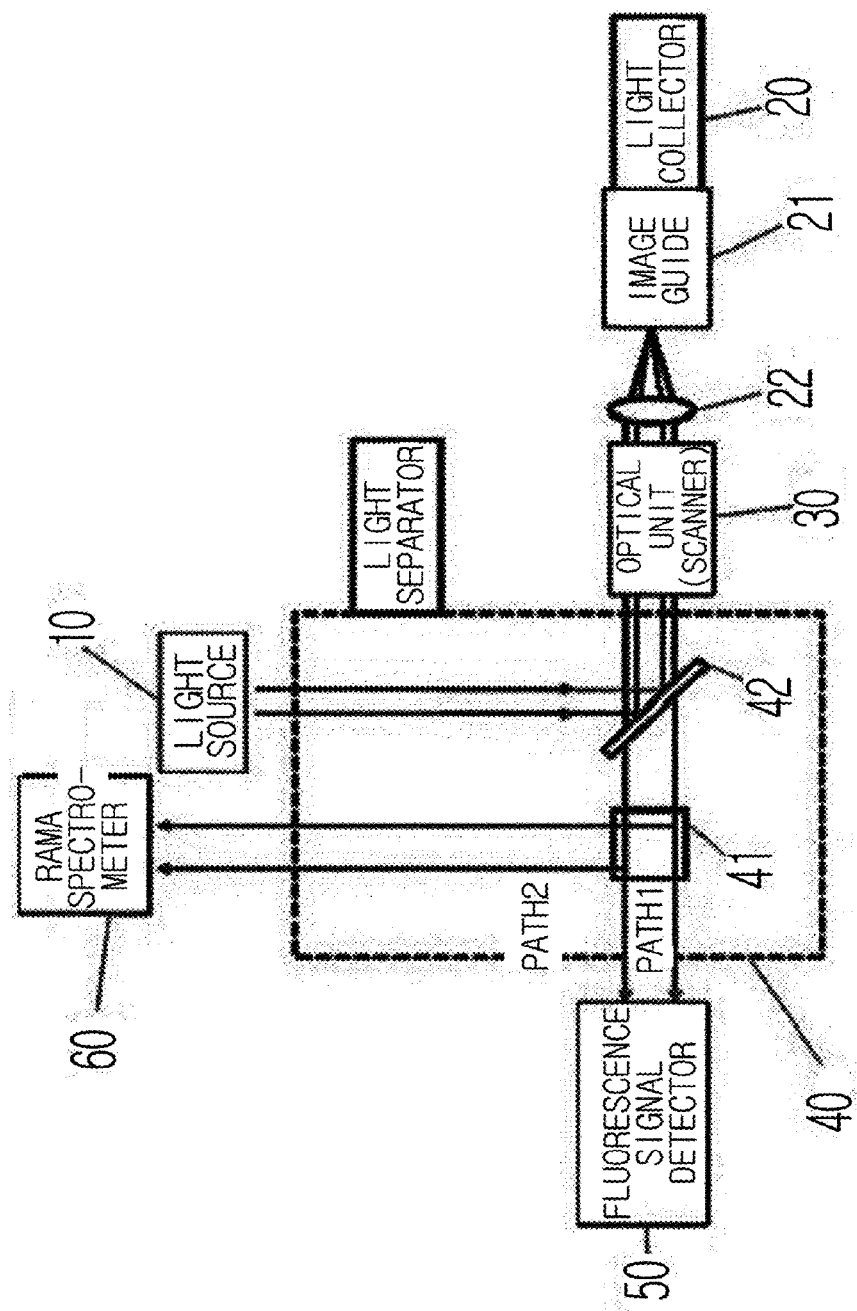
FIG. 3 is a schematic view of a constitution and an operation of a light separator of a medical imaging device for simultaneously detecting multiple fluorescence and Raman signal targets according to the present disclosure.

FIG. 3 is a schematic view provided to explain a path of an optical signal inside a medical imaging device. The medical imaging device according to one embodiment may include al light source 10, a light collector 20, an image guide 21, a scanner 30, a light separator 40, a fluorescence signal detector 50, and a Raman signal detector 60. Further, the medical imaging device may additionally include a spray means 70 to spray marker particles onto a test structure in a living organism for the diagnostic purpose.

First, the overall light path will be explained by referring to FIG. 3. The laser light 1 generated from the light source 10 is reflected from an edge filter 42, passes through a scanner 30, converged at a light emitting lens 22, transmitted to an optical fiber bundle 21, and emitted from a terminal end of the light collector 20 connected to the optical fiber bundle, that is, emitted preferably onto a test structure (T) present in a living organism. An emitted light 2 that corresponds to the wavelength of the laser light is filtered at the edge filter 42, and the filtered light is separated at a beam splitter 41 so that ½(3) is delivered to the Raman signal detector 60, while ½(4) is delivered to the fluorescence signal detector 50. The incident light 2 may be autofluorescence which is naturally emitted from the test structure (T) or fluorescence that is generated from the marker particle 300 bound to the test structure (T) in the prior injection step.

Note that it is the optical signal emitted from the marker particle 300 that is actually used for the detection of abnormal site. That is, the autofluorescence is excluded, considering a possible error due to existence of non-specific background signal that may be included. However, the autofluorescence may be advantageously used for a conventional two dimensional imaging.

The marker particle 300 may include Raman marker material which emits Raman signal and a receptor, and may also preferably include a light emitting material including fluorescence dye or quantum dot, BRET, or dye-doped silica including a complex of fluorescence dye and silica. In a preferred embodiment of the present disclosure, SERS particles utilizing surface enhanced Raman scattering effect (SERS effect) are used. Accordingly, it is possible to detect both the fluorescence signal and the Raman signals simultaneously.

To be specific, the fluorescence signal detected at the fluorescence signal detector 50 may be mainly divided into two types. One is autofluorescence which is naturally emitted from the sample itself, and the other is fluorescence signal emitted from a fluorescence dye included in the marker particle 300 according to the present disclosure. According to the present disclosure, the marker particle 300 may or may not include fluorescence dye. In the former's case, both the autofluorescence and fluorescence signal from the fluorescence dye enter, while in the latter's case, only the autofluorescence is included in the incident light. Further, in the former's case, the two dimensional imaging is implemented by use of the autofluorescence at the fluorescence signal detector 50, while the location of the test structure (T) with the marker particle 30 attached thereto is determined using the fluorescence signal originated from the fluorescence dye. Further, since the latter's case uses the autofluorescence only, the fluorescence signal detector 50 is able to perform two dimensional imaging process only. In the former's case, that is, in the case where the fluorescence dye is included in the marker particle 300, the signal from the autofluorescence is excluded from consideration in the process of detecting abnormal structure. That is, the fluorescence signal, which has relatively greater signal strength and is easier to detect, is used to determine the location of the test structure (T), i.e., determine the location of the abnormal site, while the Raman signal with narrow line width is used for the qualitative analysis on the multiple targets.

Figure 4:
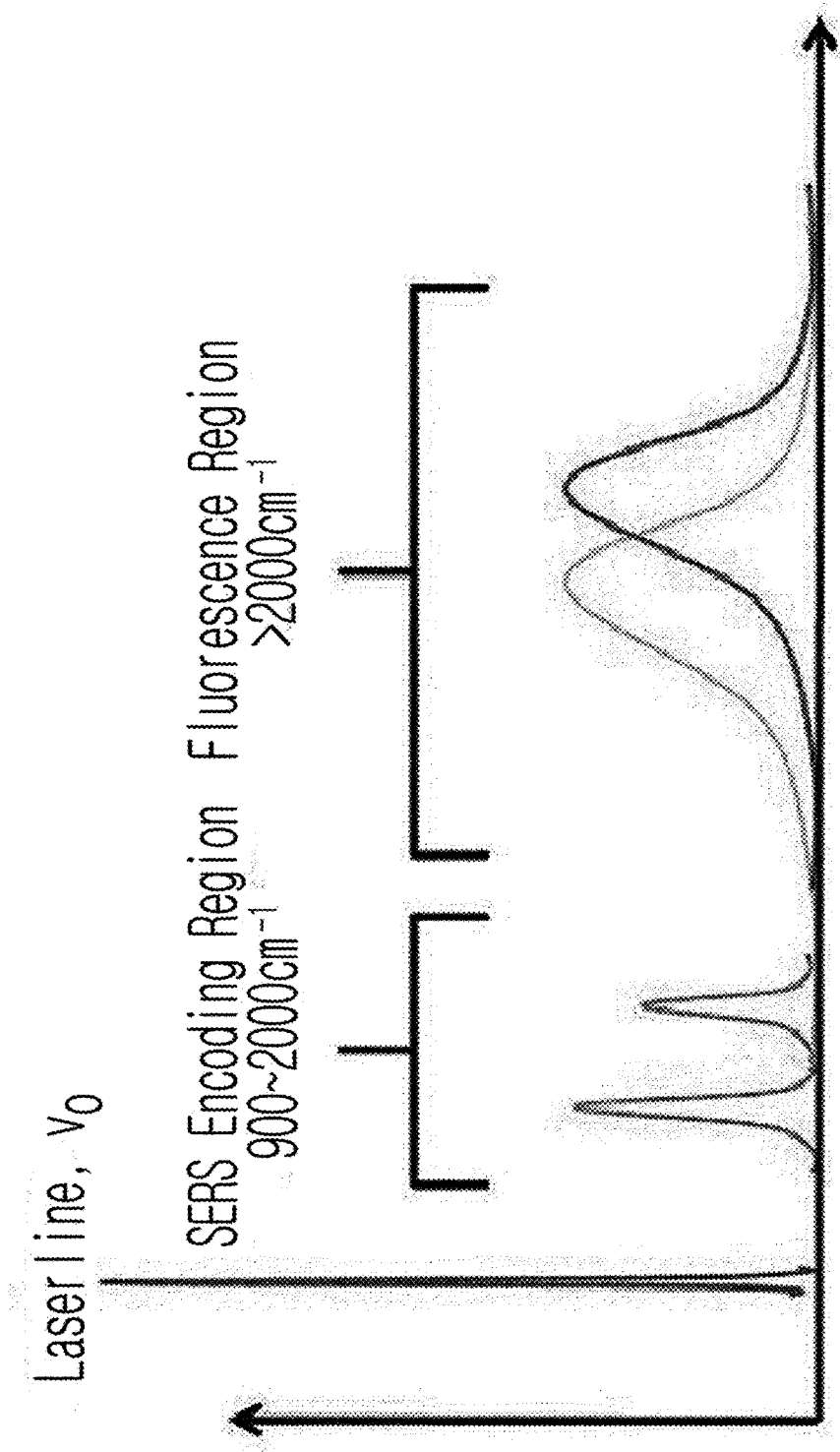
FIG. 4 is a graph schematically represents the spectrum of an optical signal generated from the marker particles 300.

FIG. 4 is a graph schematically represents the spectrum of an optical signal generated from the marker particles 300 attached to the test structure T. Referring to FIG. 4, the fluorescence signal is emitted from the fluorescence dye, and is not autofluorescence. That is, it is assumed that the marker particles 300 include fluorescence dye.

Referring to FIG. 4, the horizontal axis represents the shifting of the spectrum in the form of spectral domain (cm-1), and the vertical axis represents magnitude of the signal.

Referring to FIG. 4, the optical signal of the incident light 2 largely includes, so-called Rayleigh scattering signal region ('laser line, υ0' in the drawing), which is the direct reflective light of the laser light as emitted, Raman signals, to be specific, 'SERS encoding region', and fluorescence signal region ('Fluorescence region' in the drawing), and each spectrum shifts to the respective corresponding spectra domain and detected. That is, with reference to the laser light (i.e., Rayleigh scattering), the Raman scattering shifts about 500 to 2000 cm-1, and the fluorescence shifts about 2000 cm-1 or above (when marker particles include fluorescence dye).

The Raman band shifts from the laser wavelength (from Rayleigh scattering region) as much as the oscillation frequency of the molecule that causes Raman scattering, and such shifting spans from several tens to several thousands cm-1. Among these, the region below 900 cm-1 is not used for the detection of the Raman band by the optical fibers. Accordingly, the actually used regions among 900 to 2000 cm-1 range may be approximately 520 to 560 nm, provided that the laser wavelength is 500 nm, for example. This particular region is used to encode the Raman signals, or to be more specific, to encode the SERS signals, and the fluorescence signals use relatively longer wavelength domain. The distinction among the wavelength domains may vary, depending on the wavelength of the laser light.

In one embodiment of the present disclosure, the marker particles 300 are designed by appropriately selecting the Raman signals as explained above, or the Raman signals along with Raman marker particles and fluorescence dye to emit the fluorescence signal. That is, using the marker particles 300, it is possible to obtain a spectrum that has a sufficient difference to avoid interference of transitions of the Raman signal region and the Fluorescence signal region with respect to the laser optical signal, and it is thus possible to achieve the basic objective of the present disclosure, i.e., to separate and detect the Raman signals and fluorescence signals.

That is, since the Raman scattering does not interfere with the laser light or fluorescence, the marker particles 300 and the medical imaging device according to the present disclosure are capable of separating and detecting the Raman signals and the fluorescence signals simultaneously.

To be specific, in one embodiment of the present disclosure, among the three types of signals, the Rayleigh signals are removed by a predetermined optical filter, and the rest signals, i.e., Raman signals and fluorescence signals are separately detected so that the location of the targeted site is determined with the fluorescence signal and the targeted site is analyzed with the Raman signal. To be more specific, the fluorescence signal, which has stronger magnitude and is easier to detect, is used for the determination of the location of the test structure, while characteristics of the Raman spectrum are used for the multi in-vivo imaging in real-time basis, free of interference among the signals emitted from the multiple targets, considering the characteristics of the Raman spectrum are narrow line width, and variable shifting depending on the type of molecules used as the Raman marker material and the wavelength of the laser light. Furthermore, by implementing SERS particles as the marker particles 300, it is possible to provide the most efficient medical imaging device which compensates for the shortcoming of the Raman spectrum, i.e., weak signal strength.

In other words, since the fluorescence is used to determine the location of the test structure, while the Raman signals are used for the analysis purpose, it is not necessary to scan the wide surface area to find the Raman signals and thus is possible to find the location of the test structure in real-time basis. Further, since the Raman spectrum of the entire targeted region is recorded, simultaneous signal detection for the multiple targets is accomplished.

Further, the conventional medical imaging device constructs a two dimensional image using autofluorescence which is naturally emitted from the interior of a living organism, and thus suffered shortcoming of less accurate diagnosis because of the non-specific background signals included in the autofluorescence. The present disclosure solves the above-mentioned problem of the conventional art, by exclusively using the fluorescence signal emitted from the marker particles 300 and the Raman signals for the purpose of detecting abnormal site.

It is particularly possible to provide confocal images for more accurate diagnosis, because all of the laser light, autofluorescence naturally emitted from the sample T, and Raman signals and fluorescence signals from the marker nanoparticles 300 are passed through the same optical path.

Hereinbelow, the respective constitutions of a medical imaging device for simultaneously detecting fluorescence and Raman signals for multiple targets according to the present disclosure will be explained.

The light source 10 may emit a laser light. The light source 10 may use a gas laser, a solid state laser, or any of the known light emitting means without limitation. In one embodiment of the present disclosure, the light emitted from the light source 10 may preferably range between 400~800 nm, with resolution below 5 cm-1, and be suitable for acquisition of Raman signals. The wavelength domain may be suitably selected in consideration of the surface Plasmon resonance (SPR) with respect to precious metals such as Ag, Au included in the SERS particles used as the marker particles 300 suitable according to the present disclosure, and therefore, various solid state laser lights may be used at Ar ion laser lines of 488 and 514.5 nm, Kr-ion laser lines of 531, 568 and 647 nm, and/or at the above-mentioned domains.

The image guide 21 and the light collector 20 may include the optical fiber bundle 21, the light emitting lens 22, and various light collectors 20a-20d, to guide a laser light 1 (i.e., outgoing light) from the light source, and an optical signal 2 of an incident light emitted from the test structure, or from the marker particles 300 which are attached to the test structure and include therein Raman marker material to emit Raman signals and receptor, or additionally, fluorescence dye to emit fluorescence signals. Using the image guide 21 and the light collector 20, the laser emitted from the light source 10 can access the test structure T, and with the use of remote distance optical system, it is possible to access the targeted location with ease. If an optical fiber bundle is used as the optical collector 20b, 20c, or 20d, the heads at the terminal ends thereof may be directly manipulated or indirectly operated when connected to the endoscope according to a driving device of the endoscope. The image guide 21 and the optical fiber bundle light collectors 20b, 20c, and/or 20d may need to have suitable size for the purpose of clinical use, which may range several mm in diameter.

The optical fiber bundle may include optical fibers covered by protective layers. To acquire high resolution images, sufficient optical fibers and minimum spaces among the optical fiber cores are necessary. Generally, the optical fiber bundle may include several thousands to several hundred and thousand optical fibers which are several μm in diameter, respectively. Both ends of the optical fiber bundle 21 may be equipped with reflection-proofed glass plates to prevent reflection at both ends.

The light emitting lens 22 of the image guide 21 plays a role of converging laser lights and emitting the same to the individual optical fibers inside the optical fiber bundle, and to form a focal point that is closest as possible to the diffraction limit, the emitting lens 22 is required to keep the aberration at the minimum and also to keep from deteriorating the quality of wave front.

The scanner 30 is used to acquire confocal images by aligning paths of the outgoing and incoming lights. Accordingly, any known system may be used as the scanner 30 without limit, provided that the same forms confocal image. For example, an optical system may be used, which includes a combination of one or more mirrors and aberration-free lens to form confocal images. The examples may be found at various literatures including U.S. Pat. No. 7,447,539, U.S. Pat. No. 7,336,990 or U.S. Pat. No. 7,383,077.

The light separator 40 may include the beam splitter 41 which separates the path of the incident light into a first path and a second path and emits the light accordingly, and may additionally include the edge filter 42.

Referring to FIG. 3, the beam splitter 41 operates to divide the path of the light, which includes the Raman signal component emitted from the marker particles 300, and fluorescence signal component (autofluorescence and fluorescence originated from fluorescence dye, respectively) emitted from the test structure T or the marker particles 300, into the first and second paths 3, 4. By the separation of the light path, as explained below, the fluorescence signals are detected from the fluorescence signal detector 50 using the optical signals separated into the first path 3, while the optical signals separated to the second path 4 are used to detect the Raman signals at the Raman signal detector 60 and construct the Raman spectrum. The beam splitter 41 may be implemented as 50/50 separating cube or 50/50 separating plate.

The edge filter 42 operates to remove the laser light from the incoming light signals 2 from the scanner 30 by filtering. Because the Rayleigh light, which is the direct reflection of the emitted laser light, does not give any meaning for the analysis purpose of the test structure, these optical signals are filtered and removed. Accordingly, the present disclosure may preferably employ the edge filter 42 to perform the filtering.

The edge filter 42 may preferably have approximately 5 nm of edge steepness (when measured at optical density 6.0 wavelength and 50% transmittance wavelength) to ensure that the Rayleigh scattering is removed effectively. If the edge filter 42 is included, the light, from which the Rayleigh scattering is removed, leaving the Raman signals and fluorescence signals, arrives at the beam splitter 41 and divided into the first and second paths.

The fluorescence signal detector 50 operates to detect the fluorescence signals from the optical signals of the first path, from among the optical signals divided into each path at the beam splitter 41. The fluorescence signal detector 50 may separately include a rejection filter into the beam splitter to remove the Raman signals from the optical signal of the first path and thus to detect the fluorescence signals, by removing optical components other than the fluorescence signals. Alternatively, a band-pass filter may be included to selectively detect one or more fluorescence signals. As explained above, depending on whether the fluorescence dye is included in the marker particles 300 or not, the autofluorescence may only be detected, or fluorescence originated from the fluorescence dye may additionally be detected.

The process of exclusively extracting fluorescence signals with the functions of the edge filter 42 and the rejection filter or the band-pass filter in the medical imaging device according to the present disclosure will be explained below.

Figure 5:
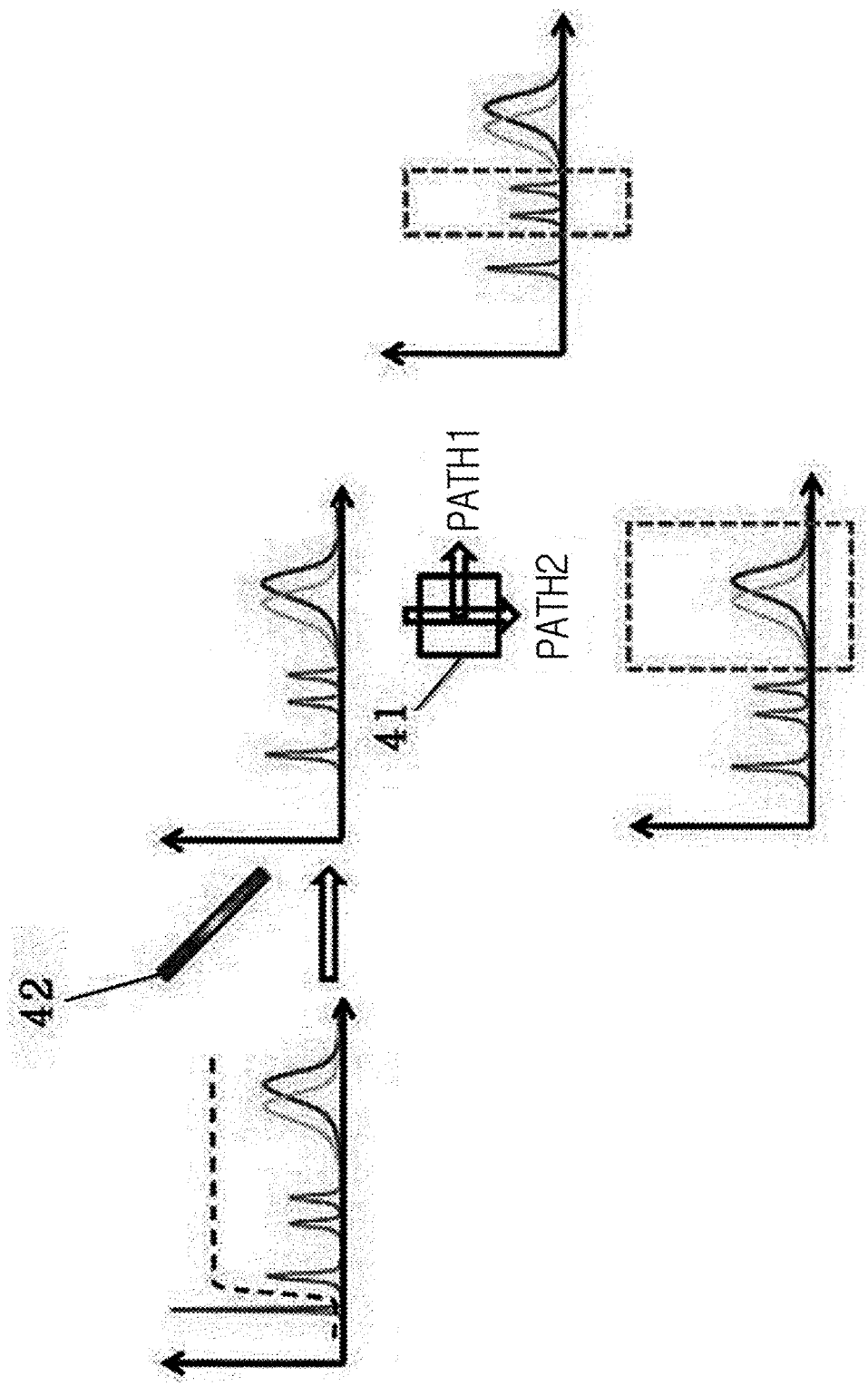
FIG. 5 is a view provided to briefly explain the process of separating and extracting the fluorescence and Raman signals only, according to the present disclosure.

FIG. 5 is a view provided to briefly explain the process of separating and extracting the fluorescence and Raman signals only. Referring to FIG. 5, it is assumed that the marker particles 300 include fluorescence dye.

Referring to FIG. 5, the optical signals emitted from the test structure include Rayleigh scattering signals (in blue) which are the direct reflection of the initial laser light from the same wavelength, Raman scattering signals (in green), and fluorescence signals (in yellow, red). As the optical signals pass the edge filter 42, only the Raman signals and the fluorescence signals remain, and therefore, the optical signals are divided into the two light paths. After that, as the optical signals advancing on the first path 4 are passed through the rejection filter or the band-pass filter, the Raman signal component is removed, thus leaving the fluorescence signals only which are detected at the fluorescence signal detector 50.

The fluorescence signal detector 50 may use, without limit, the known detector such as an avalanche photodiode or PMT which can successively accommodate the signals.

The Raman signal detector 60 plays a role of constructing the Raman spectrum by detecting the Raman scattering in the optical signals of the second path 3 which is split from the optical signals at the beam splitter 41. The Raman signal detector 60 may include a predetermined spectrometer and an optical diode array detector, or any other known signal detector, provided that the employed detector is capable of detecting Raman signals and constructing a spectrum based on the same and reading the signals. Accordingly, the optical signals of the second path 3 is formed into spectrum at the spectrometer, so that only the Raman signal region of the spectrum of the optical signal is read at a CCD or a photodiode array detector.

In another embodiment of the present disclosure, a spray means 70 may be additionally included, which sprays the marker particles 300 for the in-vivo diagnosis of the test structure using the medical imaging device.

Figure 6:
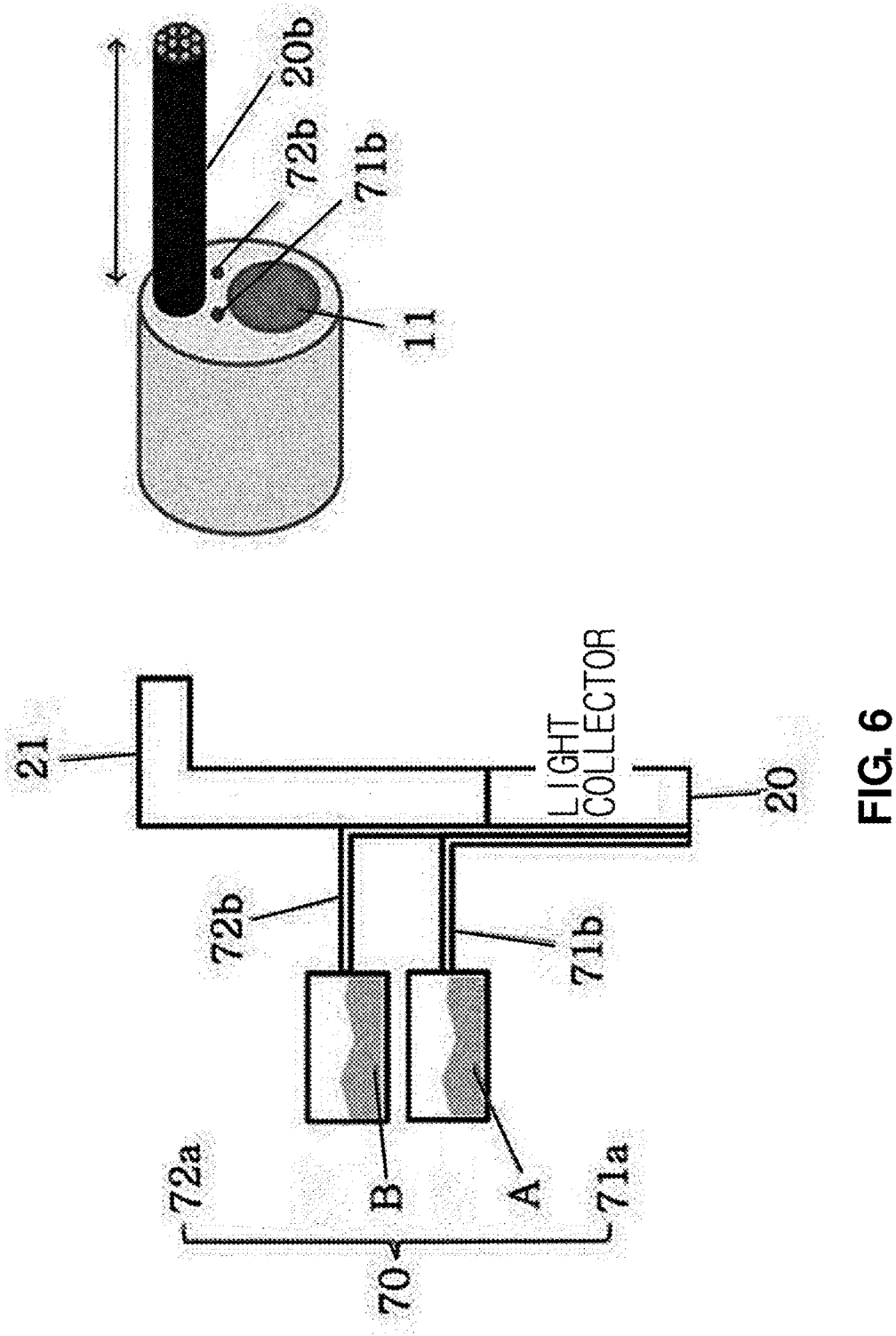
FIG. 6 illustrates an endoscopic probe implementing therein a spray means 70 according to another embodiment of the present disclosure.

Referring to FIG. 6, in one embodiment, the spray means 70 may include a particle storage tank 71a storing therein spray liquid A including the marker particles, a particle conveying pipe 71b which conveys the spray liquid A from the particle storage tank 71a to the test structure T, a washing liquid storage tank 72a storing therein washing liquid B to wash the test structure to thus remove foreign substances other than the marker nanoparticles, and a washing liquid conveying pipe 72b which conveys the washing liquid B to the test structure T.

Accordingly, as a practitioner operates a driving device 200, or uses a spray gun or the like, the liquid A for injection and the washing liquid B are sprayed from the storage tanks 71a, 72a onto the test structure through the conveying pipes 71b, 72b.

That is, with the use of the spray means 71, it is not necessary to inject the marker particles 300 into a body using needles or the like in advance, because it is possible to spray the marker particles 300 included in the injection liquid A onto the test structure in the process of conducting diagnosis with the endoscope. As a result, more accurate spraying and reduced time for diagnostic procedure are achieved.

Further, it is possible to design the spray means 71 to also spray the washing liquid B to provide clearer image of the test structure T by washing the same.

To be specific, the spray means 70 may be mounted to the heads (or probes) placed on the leading ends of the image guide 21 and the light collector 20. The endoscopic probe implementing therein the spray means 70 is illustrated in FIG. 6.

Referring to FIG. 6, the endoscopic probe may include the optical fiber bundle 20, the particle conveying pipe 71b, the washing liquid conveying pipe 72b and other endoscopic portions 11.

It is possible to use the probe of FIG. 6 to provide more accurate in-vivo diagnosis in real-time basis, with the marker particles and washing liquid conveyed through the particle conveying pipe 71b and the washing liquid conveying pipe 72b, in addition to the optical fiber bundle 20 for collecting the emitted light of the test structure T.

Next, the marker particles 300 according to the present disclosure will be explained. Basically, the marker particles according to the present disclosure include Raman marker material to emit Raman signals and receptors, and may additionally include fluorescence dye. The fluorescence dye generate fluorescence signals, and the Raman marker material generates Raman signals. Further, the receptors play a role of binding to the targeted test structure T.

According to the present disclosure, the marker particles 300 holding therein the receptors binding to specific suspected cancer cells are sprayed onto the structure where the cancer cells are present, and the medical imaging device according to the present disclosure determines location of the test structure based on the fluorescence signals generated from the fluorescence dye included in the marker particles 300 and also analyzes the presence or absence of the suspected cancer cells and properties thereof at the test structure based on the determination as to whether the Raman signals are detected or not. In an example where the fluorescence dye is not included, the Raman signals, or to be more specific, the SERS signals are used for the direct detection of the abnormal structure, while the autofluorescence is used for the imaging for observation of the structure.

That is, if the receptors of the marker particles 300 are attached to specific cancer cells, since the fluorescence signals included in the attached marker particles 300 (only autofluorescence naturally emitted from the cancer cells is detected when there is not fluorescence dye included), and fluorescence signals generated from a specific Raman marker material and Raman signal in the spectrum form are detected, it is possible to determine as to whether or not the cancer cells are present. Further, considering the very narrow line width of the Raman signal spectrum, when various receptors are bound to several marker particles 300 and injected in vivo, interference with other signals is not occurred. Therefore, it is possible to analyze Raman signals for a plurality of marker particles 300 at once. That is, it is possible to detect and analyze the signals for multiple targets.

According to the present disclosure, accurate diagnosis can be achieved, because the fluorescence signals with relatively higher strength are used to easily determine the location of the marker particles 300 attached to a specific site inside a body, while the Raman signals are used to provide accurate spectrum analysis. The marker particles 300 may be implemented in any available form such as granule, wire, or the like, provided that the same include the fluorescence dye, the Raman marker material and the receptors, and the above-mentioned basic elements may be combined with conventional marker nanoparticles such as magnetic material, radioactive isotopes, quantum dots, or photonic crystals.

The receptors may also be implemented as available ones, provided that the same specifically attach to a specific test structure. An example of the receptors may include enzymatic substrate, ligand, amino acid, peptide, protein, nucleic acid, lipid, co-factor, carbohydrate or antibody, but not limited thereto. The test structure for attachment or reaction or binding to the receptors for detection thereof, i.e., the target material may include enzyme, protein, nucleic acid, oligosaccharide, peptide, amino acid, carbohydrate, lipid, cells, cancer cells, cancer stem cells, antigen, aptamer, or other biologically-derived molecules, and more preferably, proteins related to disease, but not limited thereto.

Despite the advantages of the marker particles 300 according to the present disclosure explained above, the considerably weak signal strength of Raman signals still plays as a daunting factor for the accurate diagnosis. Accordingly, an embodiment of the present disclosure preferably uses SERS particles with enhanced Raman signal strength, and more particularly, uses F-SERS particles as the marker particles 300 including therein the fluorescence dye according to the present disclosure.

The SERS effect as used herein refers to rapid increase of Raman scattering by 103 to 1014 folds when the molecules are adhered onto the surfaces of the metallic nanoparticles such as gold, silver or copper. The SERS spectrometry based on such effect is thus gaining increasing attention for possible development of high sensitivity technology that can directly measure/analyze only one single molecule (i.e., monomer) in cooperation with the nano technology which is fast developing.

The SERS particles that can provide the SERS effect may have the form in which the Raman marker material and the receptors are added with metallic nanoparticles including one or more of silver (Ag), gold (Au) or copper (Cu) to amplify the relatively weaker Raman signals. The metallic nanoparticles may allow more incident laser beam to reach the Raman marker material, and also plays a role of an antenna which amplifies the emitted spectrum. To be specific, the SERS particles may be designed so that the Raman marker material surround the surfaces of the metallic nanoparticles, or separate cores (e.g., silica or ZnO cores) may be surrounded by metallic nanoparticles and Raman marker materials. Furthermore, the above may be formed into aggregated structure or to a wire-like structure.

For example, the SERS particles may be SOL-ID™ (Oxonica Materials Inc.) which has a structure in which silver nanoparticles as the cores are surrounded by Raman marker material and silica shells in sequence, or COINS (Composite Organic-Inorganic Nanoparticles) (NANO LETTERS, 2005, Vol. 5, No. 1, pp 49-54) including aggregates of condensed gold and silver nanoparticles in the presence of Raman organic marker material as suggested by Xing Su et al., but not limited thereto. Additionally, the SERS particles may use the particles of Korean Pat. No. 10-892629, or Korean Patent Application Publication No. 2010-0004458, or material made by binding thiol group and Raman marker material to terminus of DNA 3' and incorporating ligand to perceive specific biological substance to 5' terminus, or carbon nanotubes (KEREN et al., PNAS 2008; 105; 5844) or various other SERS particles or materials emitting strong Raman signals, but not limited thereto.

In one embodiment of the present disclosure, in addition to maximize the Raman signals using the SERS particles, it is also possible to use the F-SERS particles to which the fluorescence dye is included, to thus enable simultaneous detection of both fluorescence signals and Raman signals.

Figure 7:
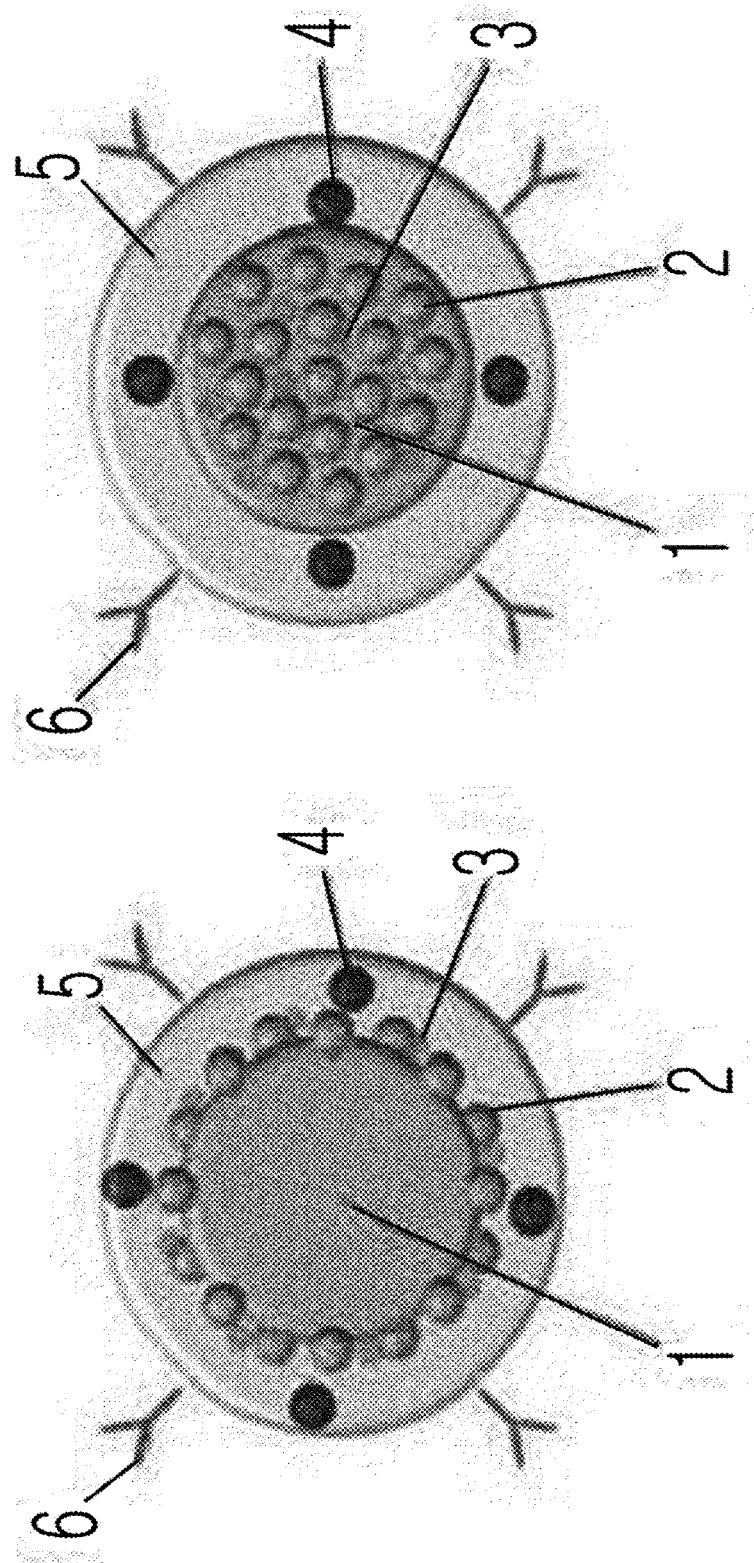
FIG. 7 illustrates the structure of F-SERS particles as an embodiment of the marker particles 300 according to the present disclosure.

FIG. 7 illustrates the structure of F-SERS particles as one embodiment of the marker particles 300 according to the present disclosure.

Referring to FIG. 7, in one embodiment of the present disclosure, the F-SERS particles have a basic structure that includes core particles 1 at the core, marker shells which surround the core particles 1 and which include metallic nanoparticles 2, Raman marker material 3 and fluorescence dye 4, and one or more antibodies 6 attached to the marker shells as one type of receptor. In addition, silica shells 5 may additionally be included, surrounding the core particles 1, the metallic nanoparticles 2, the Rana marker material 3 and the fluorescence dye 4, in which case the antibodies 6 are attached to the outer surfaces of the silica shells 5 (see FIG. 7).

The core particles 1 may include at least one of silica, silica including therein dispersed dye or silica including therein small cores of magnetic material (or radioactive isotope), metallic nanoparticles or a bundle of the same. The magnetic material may use metal or metal oxide such as CO, Mn, Fe, Ni, Gd or MM'2O4 and MxOy (where, M and M' are Co, Fe, Ni, Mn, Zn, Gd, Cr, $0<x\leq3$, $0<y\leq5$) individually or in combination. The F-SERS particles according to the present disclosure preferably use silica as the core particles 1.

The metal of the metal nanoparticles may use at least one of silver (Ag), gold (Au) and copper (Cu) that generates so-called SERS effect.

Any material including molecules to generate Raman signals may be used as the Raman marker material 3, which may be selected from a group consisting of 2-methyl benzenethiol, 4-methyl benzenethiol, 4-mercaptopyridine, 2-naphthalenethiol, 4-methoxy benzenethiol, 3-methoxy benzenethiol, 3,4-dimethylbenzenethiol, thiophenol and 3,5-methoxy dimethylbenzenethiol), or any other material that has unique SERS spectrum with high binding force with the metallic nanoparticles 2.

Organic or inorganic fluorescence dye may be used as the fluorescence dye 4, and in one example, the known organic marker material such as fluorescent rhodamine, radioactive isotope or light emitting semiconductor quantum dot such as Zn—S capped CdSe may be used. The silica shells 5 have high biocompatibility since these are harmless to human or animal body, and surface modification is easy. Therefore, the silica shells 5 can be used as the final shells.

The antibodies 6 have specific terminus to bind to specific molecule or cell. In one embodiment of the present disclosure, various antibodies 6 or other receptors may be implemented altogether, to thus induce a plurality of SERS particles, to which the receptors are applied, to emit multi-signals.

In one preferred embodiment, in selecting respective constituents of F-SERS particles as the marker particles 300, those fluorescence materials and Raman marker materials may be appropriately selected so that the fluorescence signals generated from the fluorescence dye 4 are placed at longer wavelength domain than the SERS signals generated from the Raman marker material 3, to thus avoid interference of the two signals.

The method for fabricating the SERS particles and specific characteristics thereof can be found in Korean Patent Application Publication No. 2007-0014964 filed by the inventors of the present disclosure. However, F-SERS particles are only one of examples, and other modified examples may also be implemented. For example, fluorescence particles may be incorporated into various configurations of the SERS particles explained above.

The medical imaging device for simultaneously detecting multiple fluorescence and Raman signal targets according to embodiments of the present disclosure has been explained above. Although the medical imaging device according to the present disclosure may be representatively implemented as a structure included in the endoscope to investigate test structure by being introduced into a living body, other embodiments are possible. Accordingly, the medical imaging device according to the present disclosure may be applied for various embodiments of imaging systems in addition to endoscope. For example, the medical imaging device according to the present disclosure may be implemented as a probe to accurately examine test structure of the incision in the process of surgery, or other forms of probes.

The present disclosure proposes a method for simultaneously detecting fluorescence and Raman signals for multiple targets using the medical imaging device and F-SERS particles explained above. The method for simultaneously detecting fluorescence and Raman signals of multiple targets according to one embodiment of the present disclosure may include steps of injection (S10), emitting light (S20), scanning (S30) and detecting (S40).

At injection step (S10), at least one marker particle 300 to which a plurality of various receptors are preferably attached, are injected into a body of an animal including human, in which the marker particles 300 may be injected by oral route, or by needle, or by a general injection method, or using the spray means 70 connected to the endoscopic probe as explained above.

The injection step (S20) involves emitting a laser beam into the body of the animal, in which the laser beam generated from the light source 10 is emitted to the test structure via the optical fiber bundle 21 and the optical collector 20.

At scanning step (S30), the marker particles 300 and the laser beam emitted from the test structure of the interior of the body of the animal are scanned. This step may preferably be performed by forming confocal images using the scanner 30.

That is, the light emitting step (S20) and the scanning step (S30) may be performed simultaneously. For example, using the optical fiber bundle, the laser may be emitted to the individual optical fibers within the bundle, while being scanned at the same time.

The detecting step (S40) involves separately detecting the emitted optical signals into fluorescence signals and the Raman signals, and may include, in particular, the steps of removing laser reflective light (S41), separating optical paths (S42) and separately detecting (S43).

The laser reflective light removing step (S41) includes removing, by filtering, optical component (i.e., Rayleigh light) corresponding to the laser beam from the scanned optical signals, using the edge filter 42.

The light path separating step (S42) includes separating the path of the filtered optical signals into a first path 3 and a second path 4.

The separately detecting step (S43) includes the steps of detecting fluorescence signals from the optical signals of the separated first path 3, and detecting Raman signals from the optical signals of the separated second path 4. The principles of operation are referred to the explanation provided above with reference to the medical imaging device according to the present disclosure.

With the method for simultaneously detecting fluorescence and Raman signals for multiple targets according to various embodiments of the present disclosure, real-time detection of multiple targets is possible. Particularly, because of a method for separately detecting fluorescence and Raman signals using separate marker particles, the embodiments of the present disclosure provides greatly improved advantages such as absence of non-specific background signals such as autofluorescence. Therefore, it is possible to utilize the characteristics explained above for the purpose of in vivo and in situ diagnoses using endoscopy, or image guided surgery, or the like.

Figure 8:
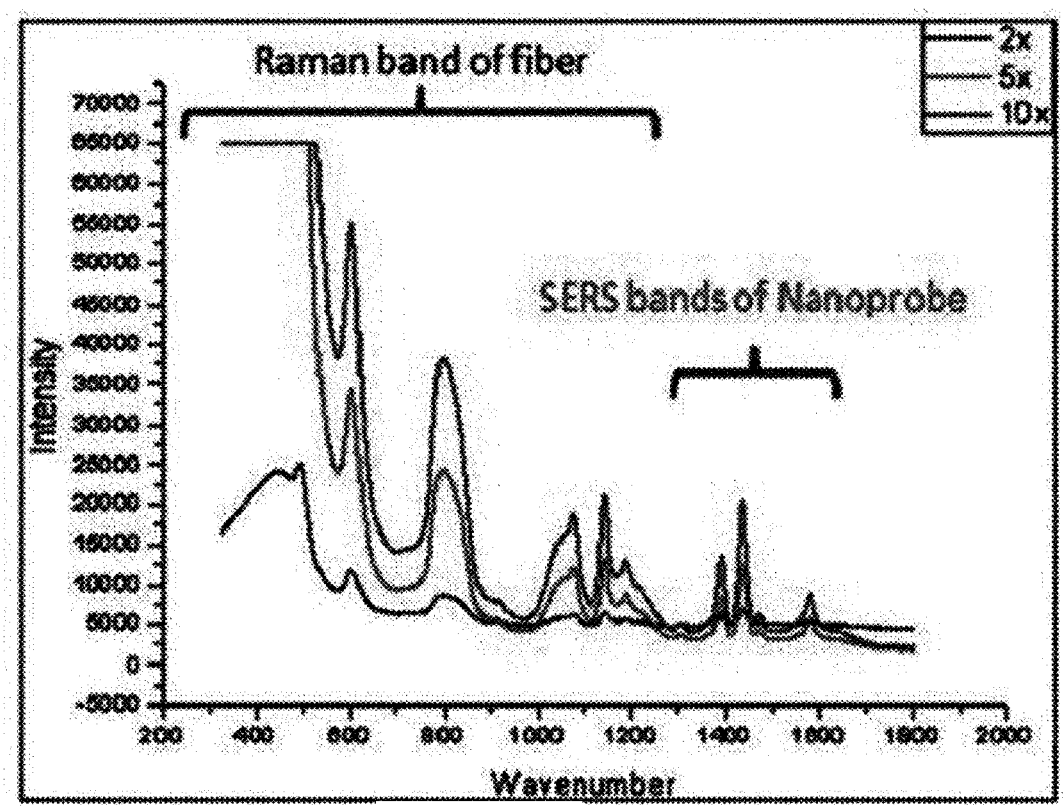
FIG. 8 shows SERS spectrum acquired using the signal detecting method and optical fiber bundle according to the present disclosure.

FIG. 8 is a SERS spectrum acquired using the signal detection method and optical fiber bundle according to the present disclosure.

Referring to the SERS spectrum of FIG. 8 measured with the optical fibers, the Raman signals naturally generated from the optical fibers are observed in the region below 900 cm-1. Accordingly, it is possible to use optical signals from the range between 900 cm-1 and 2000 cm-1 for SERS encoding.

FIGS. 9 to 14 show results of experiments conducted with the medical imaging device for simultaneous detection of multiple targets, based on the method for simultaneously detecting fluorescence and Raman signals for multiple fluorescence and Raman signal targets and medical imaging device for simultaneously detecting multiple targets using the method, according to the embodiments of the present disclosure.

As a result of experimenting with the medical imaging device prepared according to the present disclosure to simultaneously detect the multiple fluorescence and Raman signal targets, the technology of acquiring spectrum while maintaining fluorescence imaging function, enabled successful separation of paths for incident light and measure light with the use of optical fiber optical system, without having to change the optical path of the laser scanning unit, and by incorporating a combination of fluorescence imaging technology and Raman spectrometry function, the fluorescence and spectrum were measured simultaneously.

Figure 9:
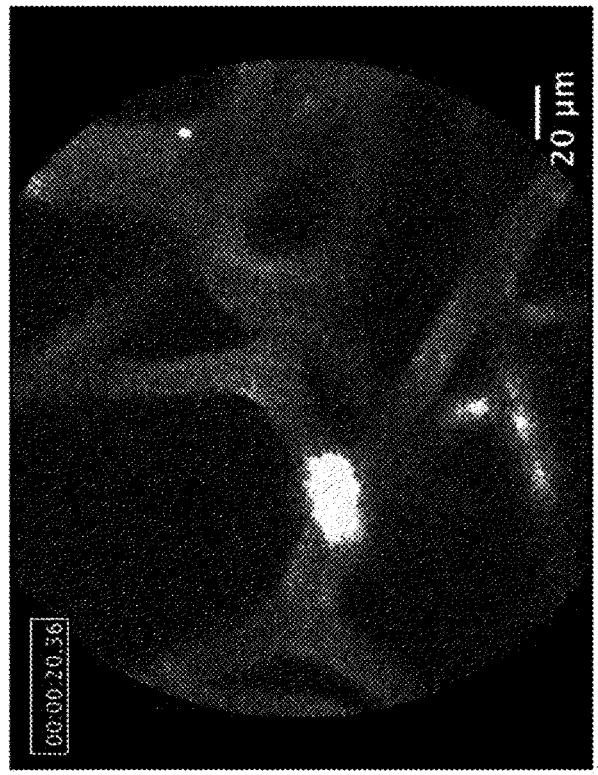
FIGS. 9 to 11 are fluorescence images taken by a medical imaging device for simultaneously detecting multiple fluorescence and Raman signal targets according to an embodiment of the present disclosure.
Figure 9:
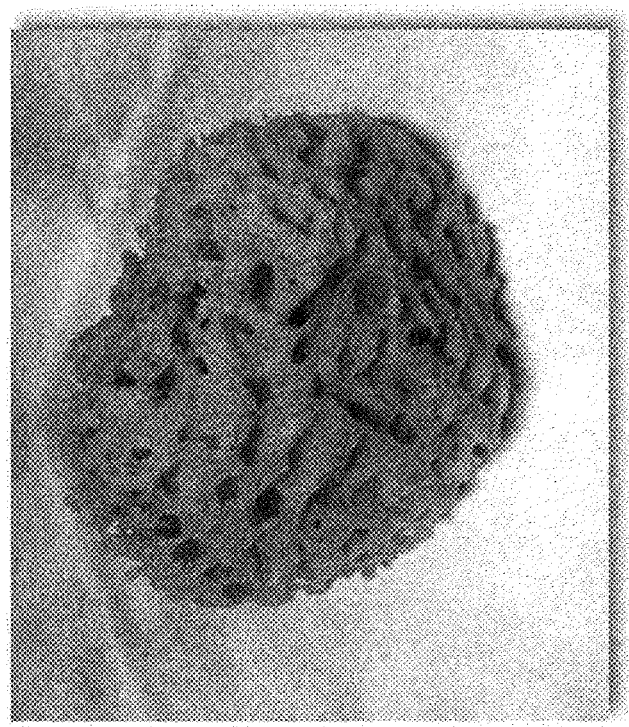
Figure 10:
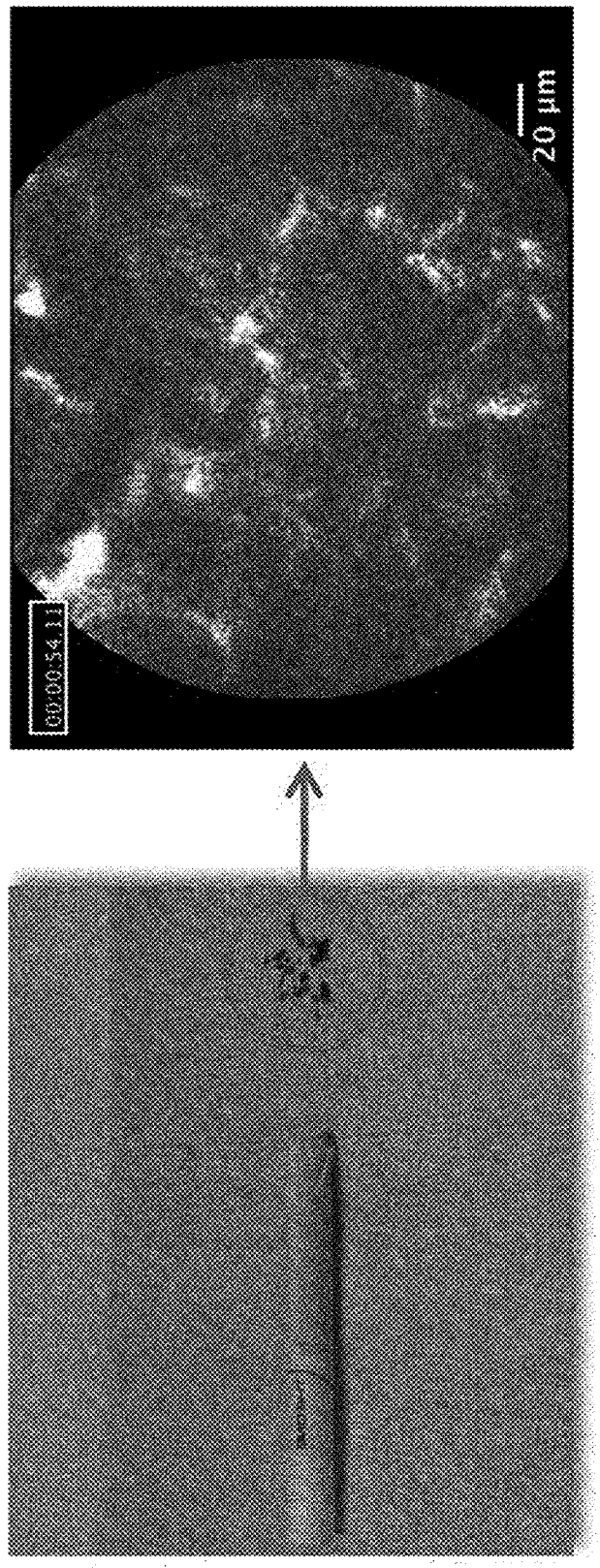
Figure 11:
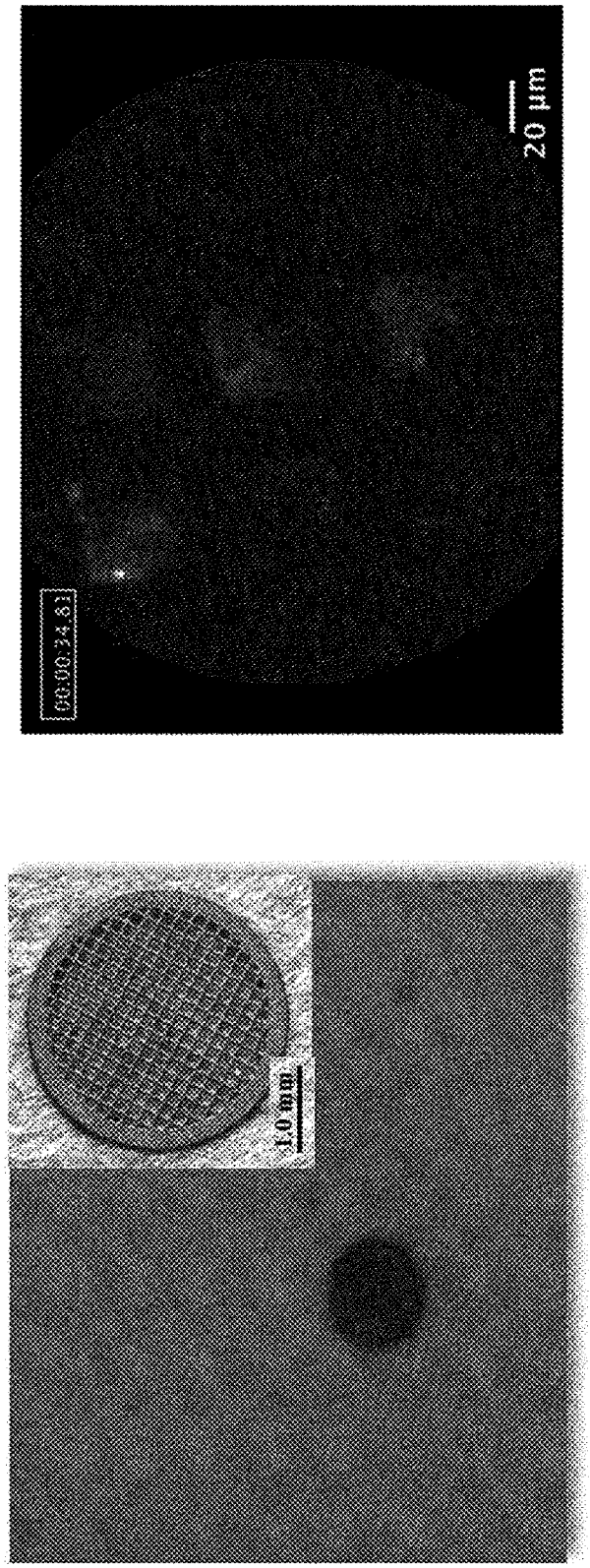

Further, FIGS. 9 to 11 are fluorescence images taken by a medical imaging device for simultaneously detecting multiple fluorescence and Raman signal targets according to an embodiment of the present disclosure, which confirm the fact that images with high resolution are acquired.

Figure 12:
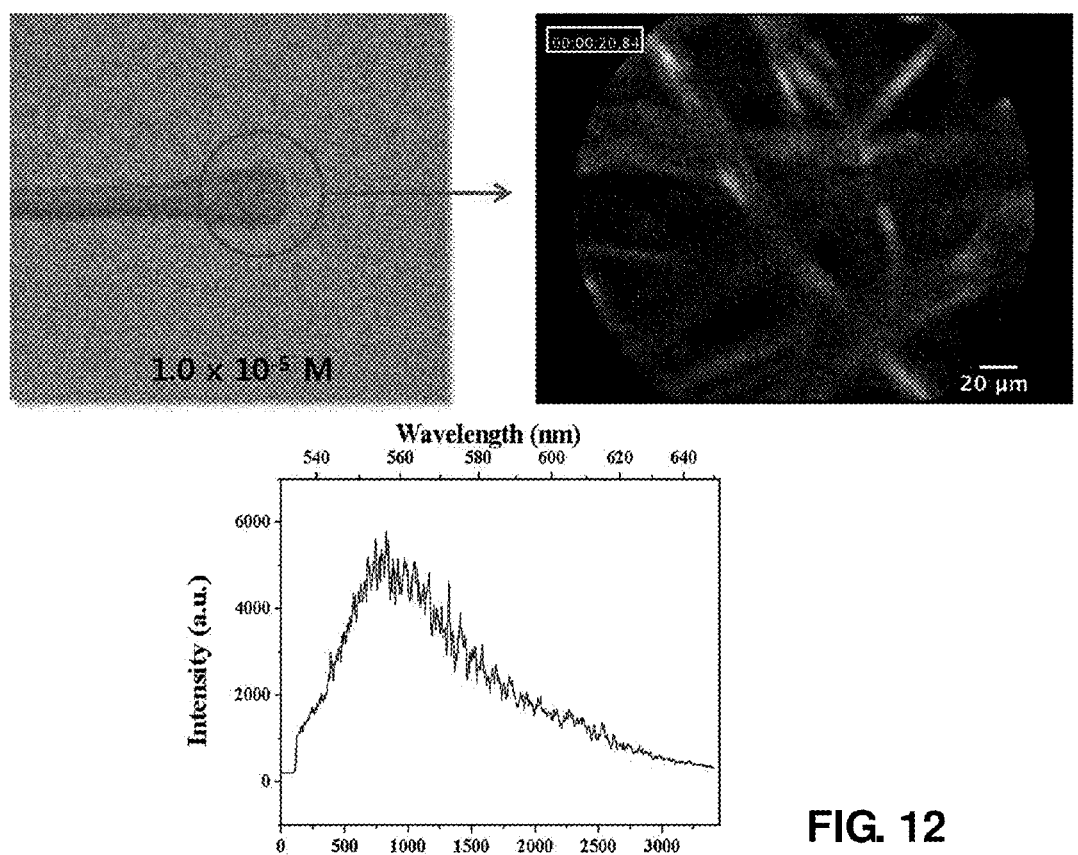
FIG. 12 provides photograph and graph representing real-time, simultaneous measure of the fluorescence and spectrum shift.

Further, FIG. 12 provides photograph and graph representing real-time, simultaneous measure of the fluorescence and spectrum shift which confirm the fact that the present disclosure can measure the fluorescence images and the spectrum at the same time and in real-time basis.

Figure 13:
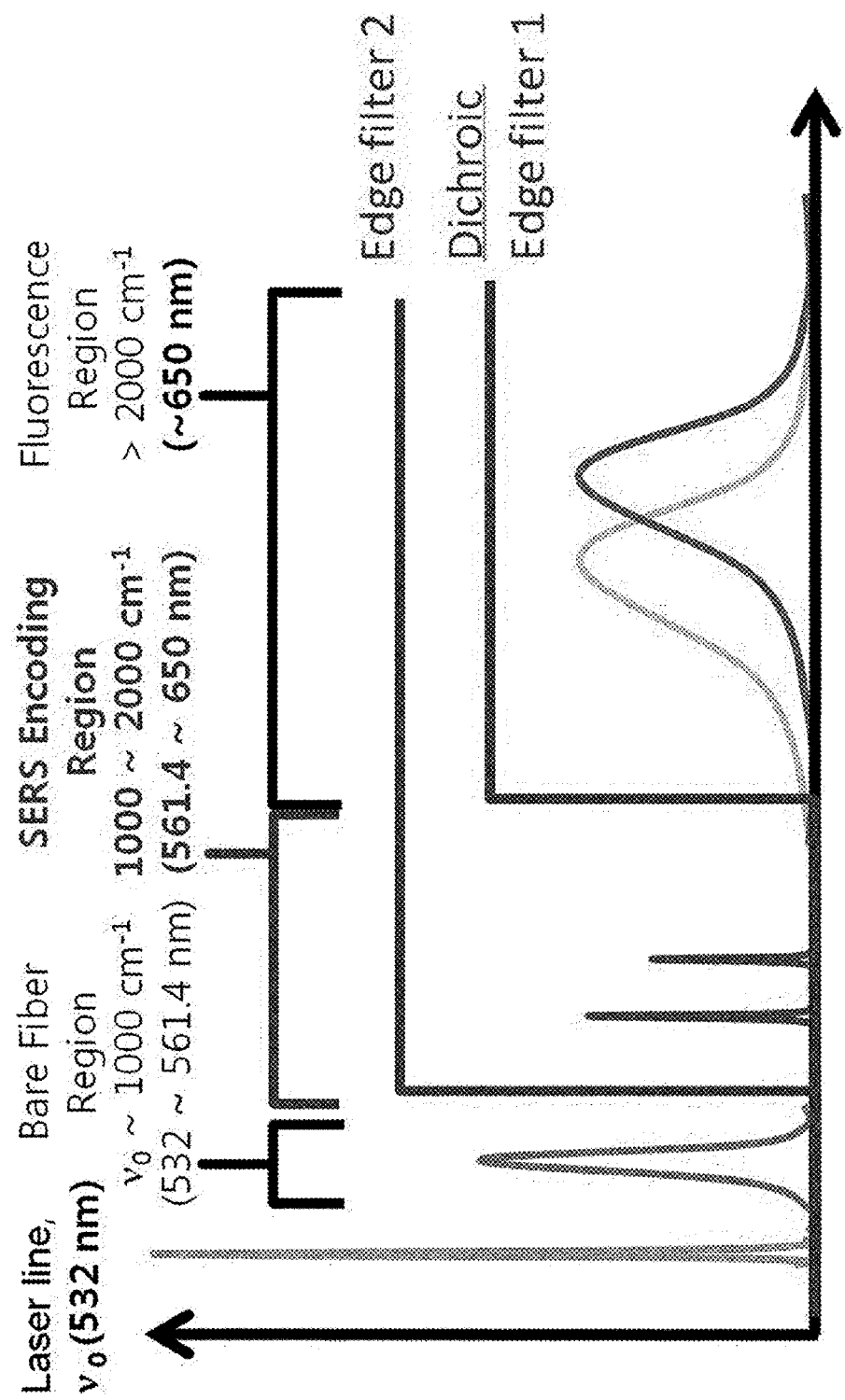
FIG. 13 are graphs for comparing optical signal domains as collected in a medical imaging device for simultaneously detecting multiple fluorescence and Raman signal targets according to an embodiment of the present disclosure.

FIG. 13 are graphs for comparing optical signal domains as collected in a medical imaging device for simultaneously detecting multiple fluorescence and Raman signal targets according to an embodiment of the present disclosure. Since the optical signals have scattering light from the laser beam itself, Raman signals naturally emitted from the optical fibers, Raman signals generated from the marker particles, and fluorescence signals are overlapped with one another, it was confirmed that by establishing an optical path, it was possible to achieve the technology to separate/collect the natural signals from the optical fiber, the Raman signals of the marker particles and the fluorescence signals.

Figure 14:
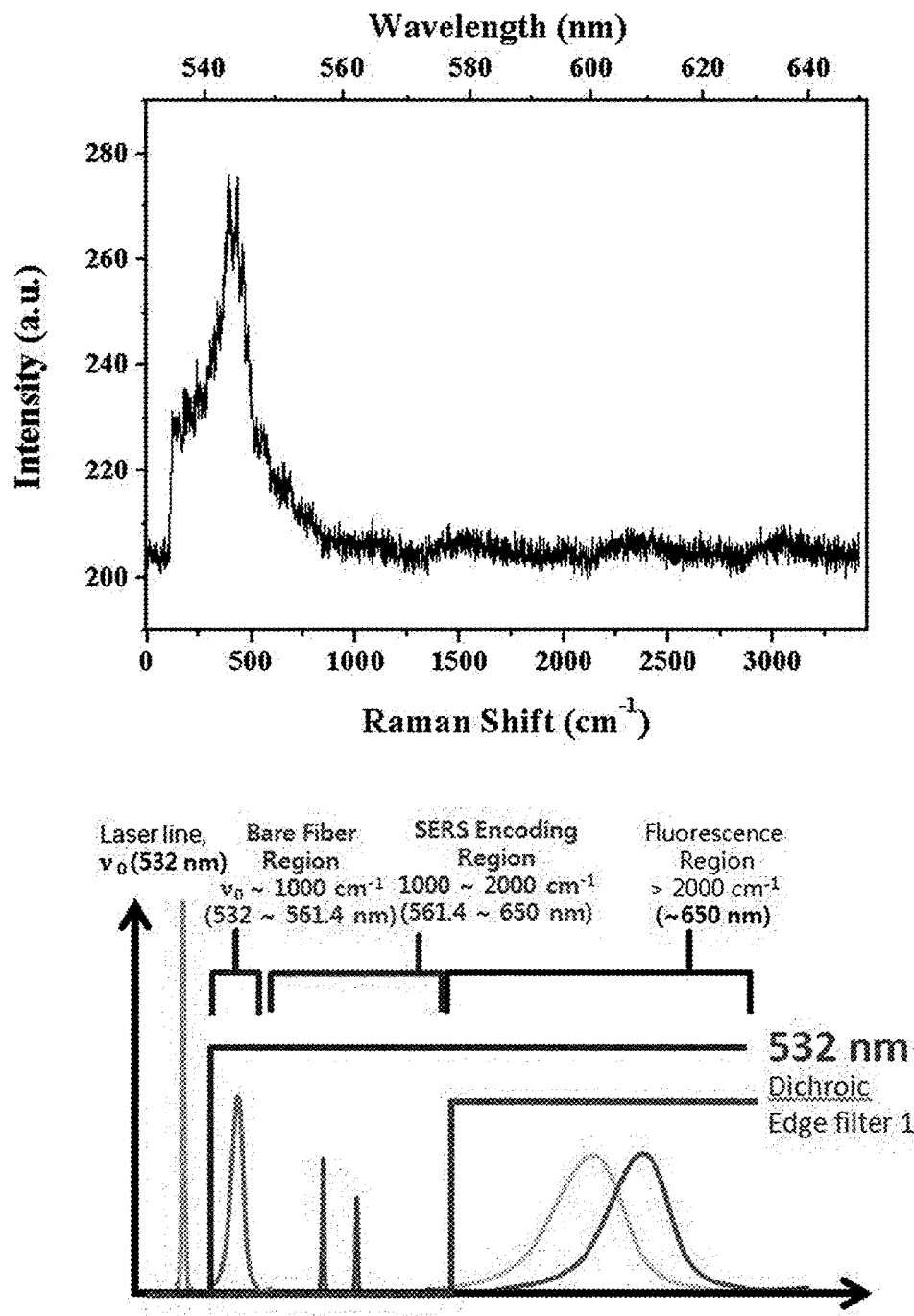
FIGS. 14 and 15 are graphs, showing when the natural Raman signals of the optical fibers are removed according to establishment of the optical path.
Figure 15:
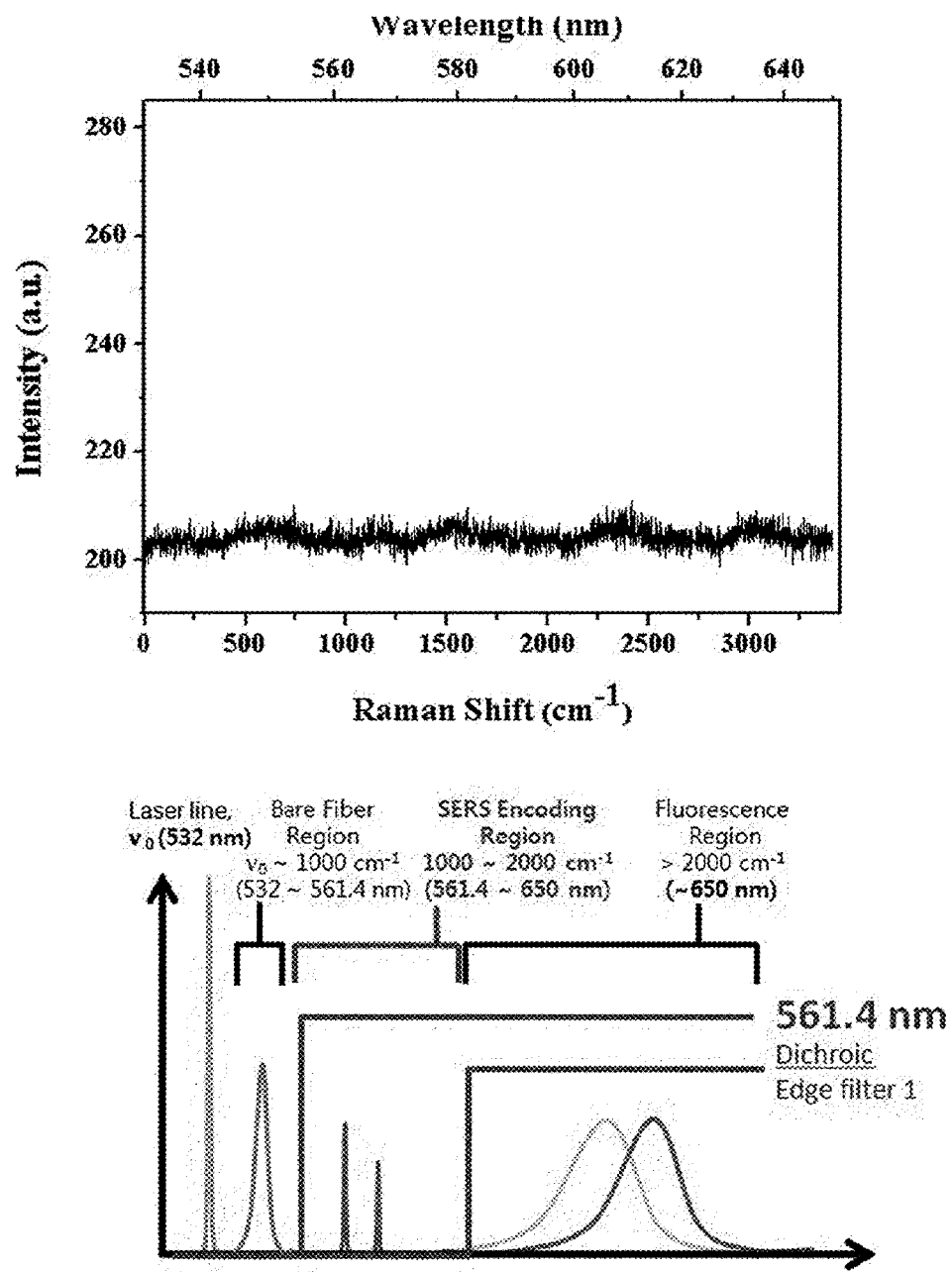

FIGS. 14 and 15 are graphs, showing when the natural Raman signals of the optical fibers are removed according to establishment of the optical path. These confirm the fact that by establishing an optical path, it was possible to achieve the technology to separate/collect the natural signals from the optical fiber, the Raman signals of the marker particles and the fluorescence signals.

Figure 16:
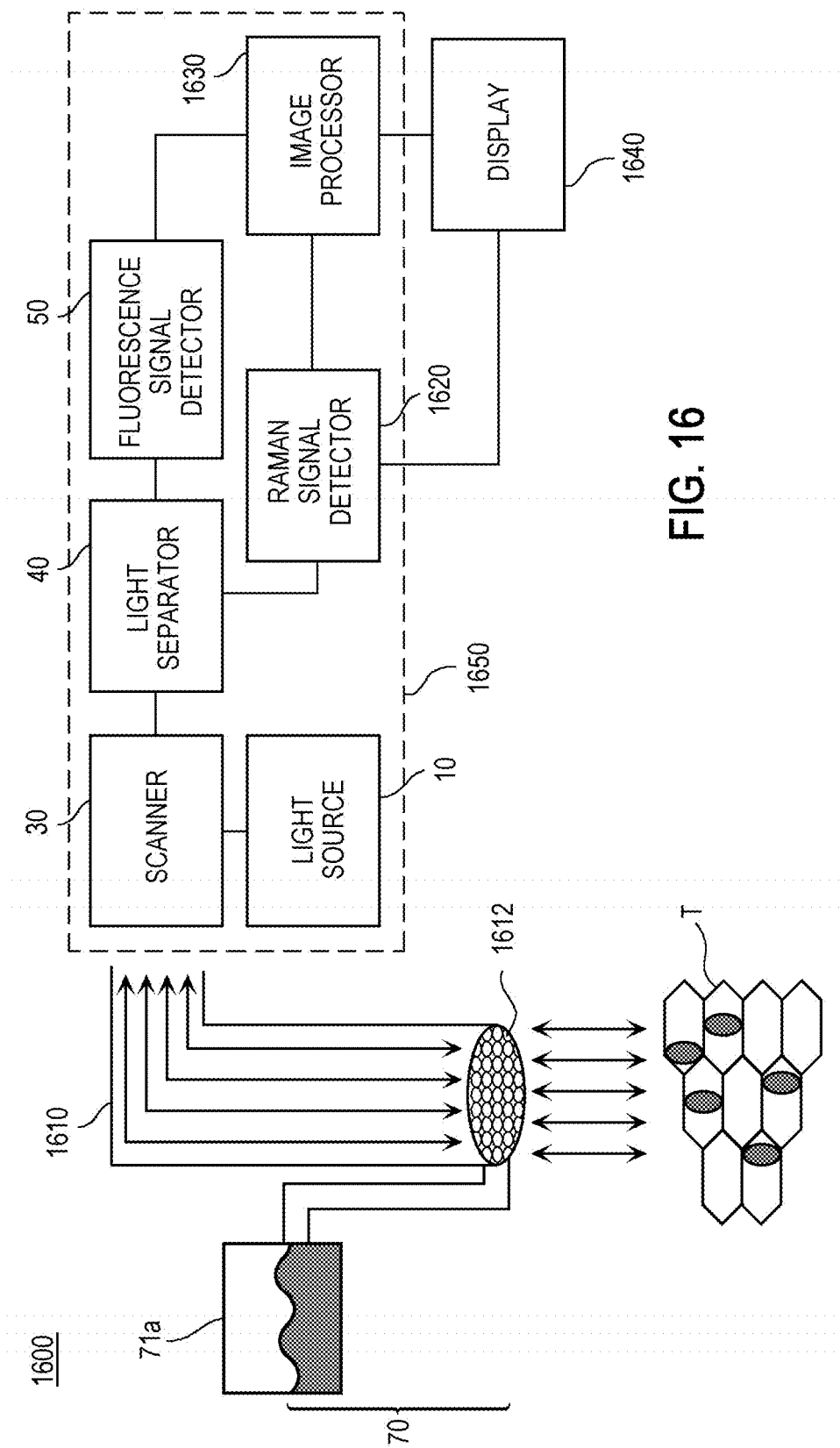
FIG. 16 illustrates a medical imaging device 1600 configured to simultaneously detect fluorescence signals and Raman signals for a plurality of targets in the test structure T according to one embodiment of the present disclosure.

FIG. 16 illustrates a medical imaging device 1600 configured to simultaneously detect fluorescence signals and Raman signals for a plurality of targets in the test structure T according to one embodiment of the present disclosure. The medical imaging device may include the storage tank 71a, the spray device 70, a probe 1610, the light source 10, the scanner 30, the light separator 40, the fluorescence signal detector 50, a Raman signal detector 1620, an image processor 1630, and a display 1640. In the illustrated embodiment, the Raman signal detector 1620 may be any signal detectors suitable for detecting Raman signals such as the Raman spectrometer 60, and may output and/or display the detected Raman signals. As described herein, the light source 10, the scanner 30, the light separator 40, the fluorescence signal detector 50, the Raman signal detector 1620, and the image processor 1630 may be collectively referred to as a signal and image processing part 1650. The test structure T may include a plurality of targets, each of which is illustrated in a hexagonal shape but is not limited thereto. In a case where the test structure T is an organic tissue inside a body of an animal, each target may correspond to a cell of the tissue. According to one embodiment, the medical imaging device 1600 may provide an image of the test structure T where the image may be defined by a plurality of pixels, as described in more detail below.

As described in more detail with reference to FIG. 6 above, the storage tank 71a may contain a plurality of marker particles, each of which may be adapted to simultaneously generate fluorescence signals and Raman signals. Each marker particle may be an F-SERS particle as illustrated in FIG. 7 and may include one or more Raman marker particles and one or more fluorescence dyes as described above. The spray device 70 may be configured to spray the plurality of marker particles from the storage tank 71a onto the test structure T such that at least one of the sprayed marker particles may be attached to one or more targets in the test structure T. Although the spray device 70 is shown as including the storage tank 71a, it may also include a driving device, a spray gun, or the like, and the storage tank 72a, the conveying pipes 71b and 72b, and/or the like.

In FIG. 16, the attached marker particles are illustrated as shaded oval shapes on the targets in the test structure T so that substructures (e.g., cells, molecules, etc.) in the test structure to which a marker particle is not attached (i.e., not indicated with shaded oval shapes) may be referred to as non-targets. As described above, the marker particles may be configured to be selectively attached to particular materials, molecules, and/or cells. For example, the marker particles may include one or more materials having high binding force with one or more particular materials, molecules, and/or cells.

As described in more detail with reference to FIGS. 1 and 2, the probe 1610 coupled to the light source 10 may include an optical fiber bundle 1612 configured to guide a laser light from the light source 10. The laser light may be emitted onto the test structure T through the optical fiber bundle 1612, which includes a plurality of optical fibers. In response to the laser light, one or more of the marker particles sprayed onto the test structure T may emit fluorescence signals and Raman signals. Further, the optical fiber bundle 1612 may be configured to simultaneously collect optical signals including the fluorescence signals and the Raman signals, which may be emitted from the targets in the test structure T.

In one embodiment, the optical fibers in the optical fiber bundle 1612 may be configured to guide the laser light and collect optical signals, from the test structure T, indicative of pixels defining an image of the test structure T. Each optical fiber is adapted to collect at least one of the optical signals indicative of a pixel among the plurality of pixels defining the image of the test structure T. For example, each optical signal collected by an optical fiber may include a fluorescence signal and a Raman signal from one or more marker particles attached to a target in the test structure T, or other signals from another source relating to a non-target in the test structure T. Further, each marker particle, which may include one or more fluorescence dyes and one or more Raman marker particles, may be configured to be attached to a specific type of target (e.g., abnormal cells, molecules, materials, etc.). In one embodiment, the at least one optical signal, which is collected by each optical fiber from the test structure T, may correspond to a pixel of the image as will be described in more detail with reference to FIG. 17 below.

As described in more detail with reference to FIGS. 1 and 3, the scanner 30 may be connected to the probe 1610 and adapted to confocally scan the collected optical signals received from the optical fiber bundle 1612. The scanner 30 may use any scanning techniques suitable for confocal microscopy. For example, each of the optical signals collected from the targets in the test structure T may have a different focal point from each other, and the scanner 30 may scan the optical signals with different focal points of the optical signals.

As described in more detail with reference to FIGS. 3 and 5, the light separator 40 may be connected to the scanner 30 and separate a path of the scanned optical signals into a first path and a second path. The first path may include the fluorescence signals in the first wavelength range, and the second path may include the Raman signals in the second wavelength. The first and second wavelength ranges may be separate from one another without mutual interference. As illustrated in FIG. 13, for example, in the case where the laser light emitted onto the test structure T has a wavelength of 532 nm, the first wavelength range may include wavelengths greater than 650 nm and the second wavelength range may include wavelengths from about 560 nm to 650 nm.

As described in more detail with reference to FIGS. 1 and 3, the fluorescence signal detector 1670 may be configured to detect the fluorescence signals in the first path. As described above, the fluorescence signals may be emitted from one or more targets to which one or more marker particles are attached, among the targets and non-targets in the test structure T. While the optical signals collected by the optical fibers in the optical fiber bundle 1632 may be indicative of all pixels defining the image of the test structure T, the detected fluorescence signals may be indicative of the pixels among the entire pixels of the image that are associated with the targets to which one or more marker particles are attached. The fluorescence signal detector 50 may provide the detected fluorescence signals, which are indicative of pixels associated with one or more targets for constructing an image of the test structure T including the targets, to the image processor for displaying the image of the test structure T.

As described in more detail with reference to FIGS. 1 and 3, the Raman signal detector 1680 may be configured to detect the Raman signals in the second path and may be further configured to construct a SERS (Surface Enhanced Raman Scattering) spectrum indicative of a property of the plurality of targets in the test structure T based on the detected Raman signals. For example, the SERS spectrum may be generated and/or displayed in a wavelength domain, a wavenumber domain, or any other domains that may be suitable to represent a spectrum of Raman signals. In one embodiment, the Raman signal detector 1620 may display the SERS spectrum directly, or provide the SERS spectrum to the image processor 1630 or to the display 1640.

As described in more detail with reference to FIGS. 8 and 13-15, the SERS spectrum constructed from the Raman signals may indicate the types of the targets to which one or more marker particles are attached. For example, the types of targets (e.g., types of abnormal cells, molecules, etc.) may be distinguished by using Raman marker materials, each of which emits a Raman signal having a particular wavelength with a narrow line width associated with a particular type of target in response to a laser light. Accordingly, each Raman signal at a particular wavelength in the SERS spectrum may indicate a specific type of target to which the corresponding Raman marker particle is configured to be attached for emitting the Raman signal.

As described in more detail with reference to FIGS. 8 and 13-15, the SERS spectrum constructed from the Raman signals may indicate relative amounts of the targets to which one or more marker particles are attached. For example, the intensity of Raman signals in the SERS spectrum may indicate relative amounts of the Raman marker particles corresponding to the Raman signals. That is, if the number of a particular type of Raman marker particles (as included in the marker particles) attached to the targets increases, the intensity of the Raman signal corresponding to the particular type of Raman marker particle increases.

In one embodiment, the SERS spectrum constructed from the Raman signals may indicate morphological characteristics of the targets to which one or more marker particles are attached. For example, the targets may be cells in an organic tissue undergoing apoptosis. As used herein, apoptosis may refer to a process of cell death that may occur in multicellular organisms. Apoptosis may involve morphological changes such as blebbing, cell shrinkage, nuclear fragmentation, chromatin condensation, chromosomal DNA fragmentation, and global mRNA decay. In this embodiment, particular materials configured to be selectively attached to a cell undergoing apoptosis (e.g., a cell undergoing morphological changes) may be used as the marker particles. A Raman marker particle included in such marker particles may emit a Raman signal having a particular wavelength in response to a laser light when attached to a cell undergoing apoptosis. As such, the Raman signal at the particular wavelength in the SERS spectrum may indicate morphological characteristics (e.g., morphological changes) of the target.

The image processor 1630 may be configured to receive the fluorescence signals from the fluorescence signal detector 50 and the Raman spectrum from the Raman signal detector 1620. Based on the received fluorescence signals and/or Raman spectrum, the image processor 1630 may construct an image of the test structure T indicative of locations of the plurality of targets and/or an image indicative of at least one property of the targets in the test structure T. In one embodiment, the image processor 1630 may generate a single image by overlaying or combining the images indicative of the locations and property of the targets. In another embodiment, the image processor 1630 may generate a single image configured with two display sections for separately displaying the images indicative of the locations and property of the targets. The display 1640 is configured to receive the image from the image processor 1630 and display the image. In the case of receiving the Raman spectrum directly from the Raman signal detector 1620, the display 1640 may display the Raman spectrum.

Figure 17:
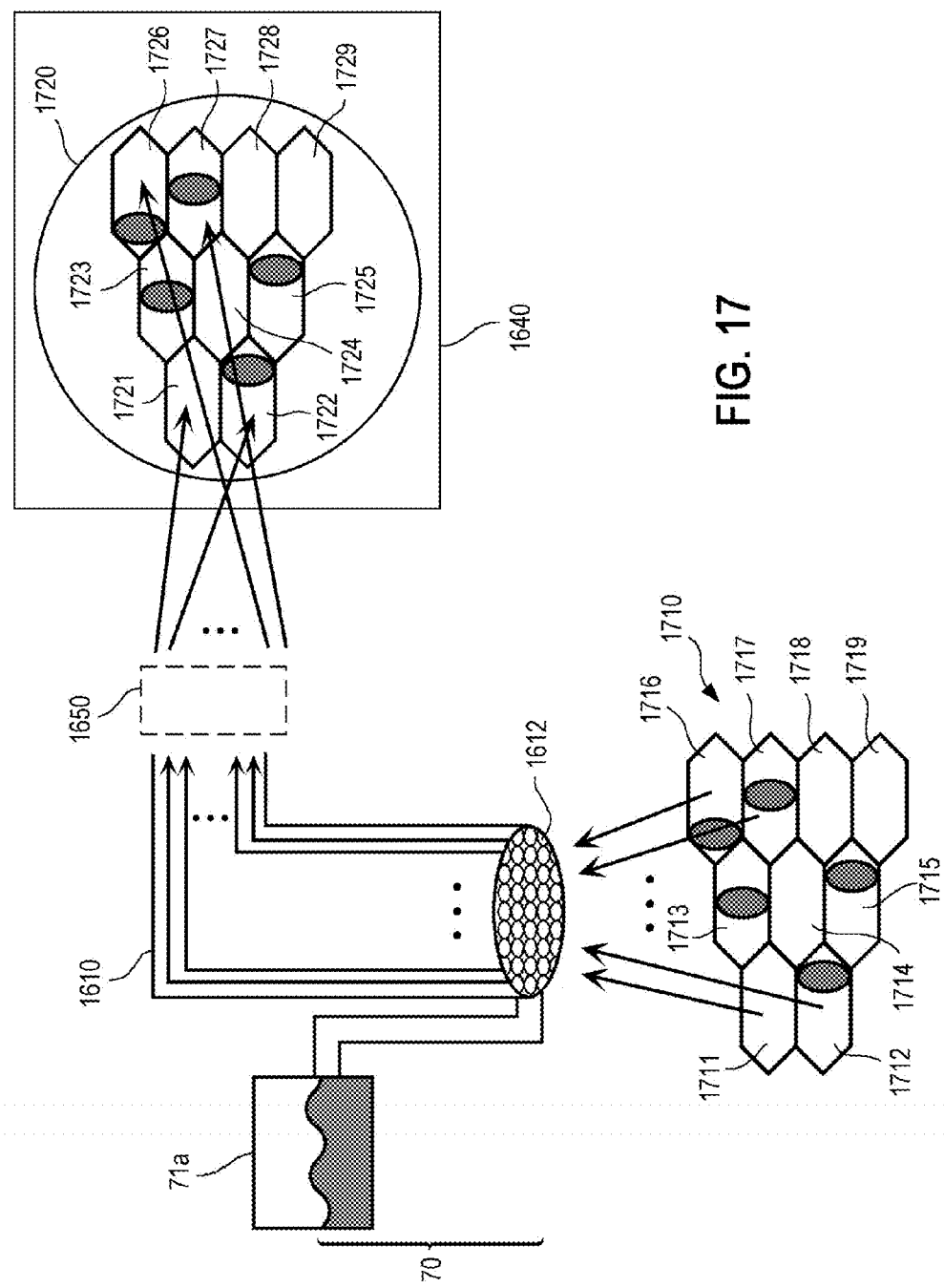
FIG. 17 illustrates the medical imaging device 1600 that generates a fluorescence image 1720 of a test structure 1710 from the optical signals collected via the optical fiber bundle 1612 according to one embodiment of the present disclosure.

FIG. 17 illustrates the medical imaging device 1600 that generates a fluorescence image 1720 of a test structure 1710 from the optical signals collected via the optical fiber bundle 1612 according to one embodiment of the present disclosure. Since the medical imaging device 1600 has been described in detail with reference to FIGS. 3 and 16, the individual parts or units of the signal and image processing part 1650 (i.e., the light source 10, the scanner 30, the light separator 40, the fluorescence signal detector 50, the Raman signal detector 1620, and the image processor 1630) are omitted in FIG. 17. The generated fluorescence image 1720 may be displayed on the display 1640 along with and/or in combination with the Raman spectrum.

The test structure 1710 may be, for example, the test structure T as described above and may include a plurality of substructures 1711 to 1719. In the illustrated embodiment, a plurality of marker particles may be sprayed from the spray device 70 and one or more marker particles may be attached to one or more substructures 1711-1719 in the test structure 1710. For example, a marker particle as indicated with a shaded oval shape may be attached to each of the targeted substructures 1712, 1713, 1715, 1716, and 1717, which may be referred to as "targets" in the test structure 1710. The other substructures 1711, 1714, 1718, and 1719, to which a marker particle is not attached, may be referred to as "non-targets" in the test structure 1710.

When a laser light is emitted onto the test structure 1710 through the optical fibers in the optical fiber bundle 1612, the substructures 1711-1719 may emit optical signals. In the case of the targets (i.e., the targeted substructures), each of the marker particles attached to the targets 1712, 1713, 1715, 1716, and 1717 may emit a fluorescence signal (and a Raman signal). Each of the fluorescence signals and Raman signals from the marker particles attached to the targets 1712, 1713, 1715, 1716, and 1717 may be associated with a pixel and collected via an optical fiber in the optical fiber bundle 1612. On the other hand, the non-targets 1711, 1714, 1718, and 1719 may emit optical signals (e.g., a reflected optical signal, autofluorescence signals, native Raman signals, etc.) other than the fluorescence signals or the Raman signals that may be emitted from marker particles in response to the laser light. In this case, each of the optical signals from the non-targets 1711, 1714, 1718, and 1719 may be associated with a pixel and collected via an optical fiber in the optical fiber bundle 1612. In this manner, the optical fibers in the optical fiber bundle 1612 may collect signals corresponding to a plurality of pixels defining the fluorescence image 1720. The number of optical fibers in the optical fiber bundle 1612 may be configured to match a desired number of pixels in the fluorescence image (i.e., image resolution). In one embodiment, the fluorescence image may have an image resolution of 5 to 10 um. In another embodiment, the fluorescence image may have an image resolution less than 20 um.

As described above with reference to FIG. 16, the signal and image processing part 1650 may scan, separate, and detect the collected fluorescence signals and Raman signals from the targets 1712, 1713, 1715, 1716, and 1717, and, based on the detected fluorescence signals and Raman signals, generate pixel data associated with the targets 1712, 1713, 1715, 1716, and 1717. Further, the signal and image processing part 1650 may generate pixel data associated with the non-targets 1711, 1714, 1718, and 1719 based on the optical signals from the non-targets 1711, 1714, 1718, and 1719. The signal and image processing part 1650 may then construct the fluorescence image 1720 of the test structure 1710, 1713, 1715, 1716, and 1717 and provide the image 1720 to the display 1640 for output. Since the fluorescence image is generated based on the pixels associated with fluorescence signals emitted from the marker particles attached to the targets and other signals emitted from the non-targets, the fluorescence image may distinguish between the pixels associated with the targets and the pixels associated with non targets. In this manner, the locations of the targets 1712, 1713, 1715, 1716, and 1717 in the test structure 1710 may be indicated or identified in the fluorescence image 1720.

Although the display 1640 is shown to display the fluorescence image 1720, the display 1640 may also display a Raman image along with or in combination with the fluorescence image 1720. For example, the signal and image processing part 1650 may generate a Raman image indicative of at least one property of the targets 1712, 1713, 1715, 1716, and 1717 in the test structure 1710. In one embodiment, the Raman image may be a Raman spectrum, which may include an indication of one or more properties of the targets. In another embodiment, the Raman image may be indicated in the fluorescence image by marking or designating (e.g., highlighting, numbering, etc.) one or more properties of the targets for the pixels associated with the targets.

Figure 18:
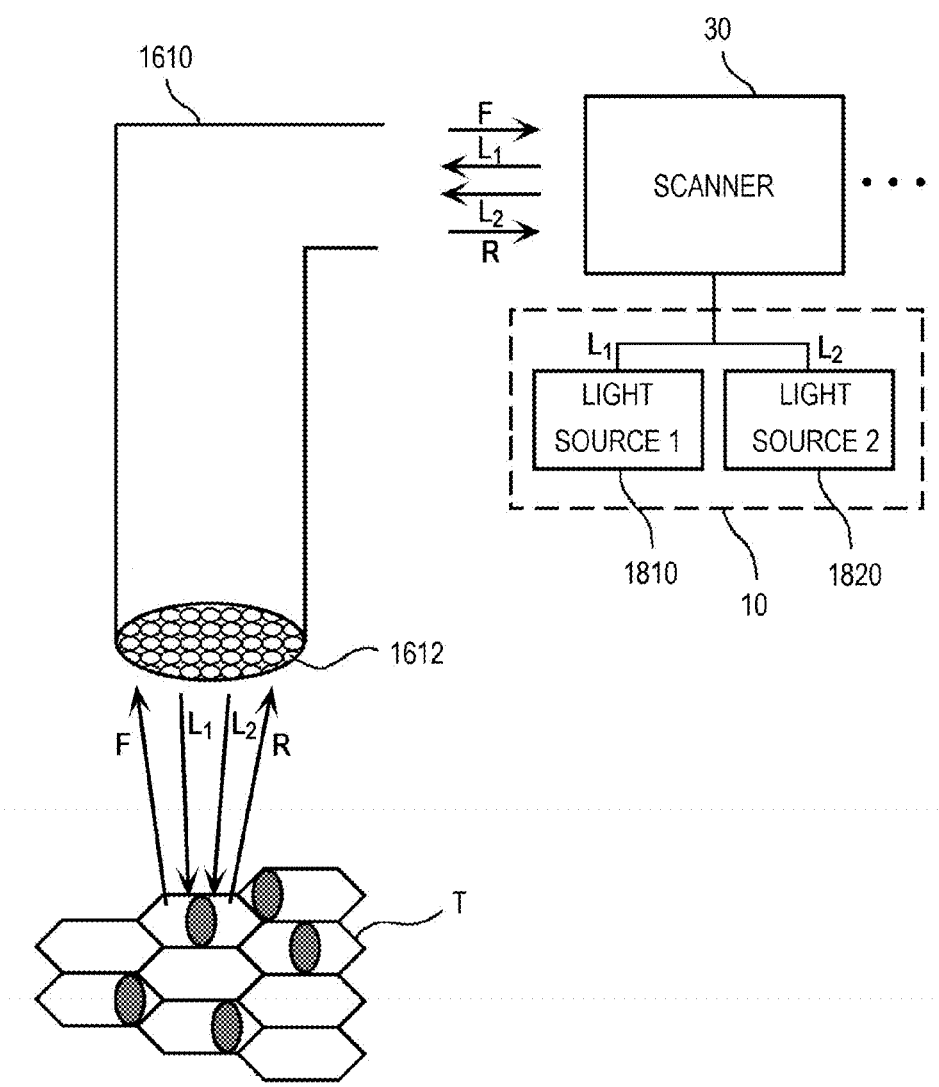
FIG. 18 illustrates the medical imaging device 1600 that includes a first and a second light source 1852 and 1854 as the light source 10 in FIG. 16 according to one embodiment of the present disclosure.

FIG. 18 illustrates the medical imaging device 1600 that includes a first and a second light source 1852 and 1854 as the light source 10 in FIG. 16 according to one embodiment of the present disclosure. In the medical imaging device 1600, the first light source 1852 and the second light source 1854 may be configured to generate a first laser light L1 and a second laser light L2, respectively, where the first and the second laser light have different wavelengths. Alternatively, any suitable number of light sources configured to generate laser lights with different wavelengths may be used as the light source 10 in the medical imaging device 1600. In such cases, a plurality of light sources may be used as the light source 10 to generate laser lights having two or more laser wavelengths while using the same parts or units other than the light source 10 in the medical imaging device 1600. The plurality of laser lights with two or more wavelengths may be simultaneously or sequentially emitted via the scanner 30 and the optical fiber bundle 1612 onto the test structure T. The wavelengths for the plurality of light sources may be associated with a plurality of types of fluorescence dyes and/or a plurality of types of Raman marker particles (e.g., materials), such that each wavelength may be adapted to cause or trigger one or more types of the fluorescence dyes and/or one or more types of the Raman marker particles to emit one or more fluorescence signals and/or one or more Raman signals in response to a laser light with the wavelength.

In the case of using the first light source 1852 and the second light source 1854, the first laser light L1 may have a first wavelength that may cause or trigger one or more types of fluorescence dyes in one or more marker particles to emit the fluorescence signals in response to the first laser light L1. Further, the second laser light L2 may have a second laser wavelength that may cause one or more types of Raman marker particles in one or more marker particles to emit the Raman signals in response to the second laser light. The first and second wavelengths of the first and second laser lights may fall within the visible light zone or the near infra-red zone, which may not damage the body of an animal including human.

In some embodiments, the first and the second wavelengths of the first laser light L1 and the second laser light L2, respectively, may range between 400 nm and 800 nm, and the range of the first wavelength may be shorter or longer than the range of the second wavelength. In one embodiment, the first wavelength of the first laser light L1 may range between 400 nm and 600 nm and the second wavelength of the second laser light L2 may range between 600 nm and 800 nm. In another embodiment, the first wavelength of the first laser light L1 may range between 600 nm and 800 nm and the second wavelength of the second laser light L2 may range between 400 nm and 600 nm. Using a plurality of laser light sources capable of generating laser lights having multiple wavelengths that are adapted to a variety of types of fluorescence dyes and/or Raman marker particles, the number of materials that can be used as fluorescence dyes and/or Raman marker particles may increase without being limited to using a single laser light where materials for a fluorescence dye and a Raman marker particle are both responsive to the laser light of a specified wavelength.

In case of using fluorescence dyes and/or Raman marker particles inside a human body for an in-vivo diagnosis in various jurisdictions, only the materials approved by a corresponding health authority, such as Food and Drug Administration ("FDA"), European Medicines Agency ("EMA"), or the like, may be used. If a single light source emitting a light of a single wavelength is used, the number of authorized materials for fluorescence dyes and/or Raman marker particles, which can respond to the same wavelength, may be limited. Thus, using a plurality of laser light sources with a plurality of wavelengths, which can cause or trigger one or more types of fluorescence dyes and/or Raman marker particles to emit the fluorescence and/or Raman signals, may provide an advantage of enlarging or expanding the number or variety of choices for authorized materials that can be used as fluorescence dyes and/or Raman marker particles.

In the case of materials for fluorescence dyes, any material approved by an authorized health agency may be used so long as the material can emit a fluorescence signal with a wavelength not overlapping with that of another fluorescence signal and/or a Raman signal from another fluorescence dye or a Raman marker particle, which may be used together with the material. For example, at least one of Fluorescein, Protoporphyrin IX (PpIX), Indocyanine Green (ICG), and/or Methylene Blue (MB), which are approved by FDA, may be used as fluorescence dyes. For instance, Fluorescein may emit a fluorescence signal with a wavelength of about 512 nm in response to a laser light having a wavelength of about 494 nm, Protoporphyrin IX may emit a fluorescence signal with a wavelength of about 635 nm in response to a laser light having a wavelength of about 405 nm, Indocyanine Green may emit a fluorescence signal with a wavelength of about 830 nm in response to a laser light having a wavelength of about 800 nm, and Methylene Blue may emit a fluorescence signal with a wavelength of about 680 nm in response to a laser light having a wavelength of about 660 nm. In the case of materials for Raman marker particles, any material approved by an authorized health agency may be used so long as the material can emit a Raman signal with a wavelength not overlapping with that of a fluorescence signal and/or another Raman signal from a fluorescence dye or another Raman marker particle, which may be used together with the material.

The foregoing embodiments and advantages are merely exemplary and are not to be construed as limiting the present disclosure. The present teaching can be readily applied to other types of apparatuses. Also, the description of the exemplary embodiments of the present inventive concept is intended to be illustrative, and not to limit the scope of the claims, and many alternatives, modifications, and variations will be apparent to those skilled in the art.

The present disclosure is industrially applicable, since it relates to a medical imaging device including an endoscope employing therein optical fiber bundle probe for use in the in-vivo disease diagnosis of an animal including human, an optical fiber probe, or a remote distance optical system, and a method for detecting signals that may be used in a method for in-vivo diagnosis using the said medical imaging device.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

ASPECTS OF THE PRESENT DISCLOSURE

Hereinafter, some aspects of the present disclosure will be additionally stated.

Example 1

According to an aspect of the present disclosure, there is provided a method for simultaneously detecting, by a medical imaging device, fluorescence signals and Raman signals for multiple targets in a test structure inside a body of an animal. The method may comprise a step of directly spraying a plurality of marker particles onto the test structure. In this method, each marker particle may be adapted to simultaneously generate fluorescence signals in a first wavelength range and Raman signals in a second wavelength range and include one or more Raman marker particles, receptors, one or more fluorescence dyes and one or more metallic nanoparticles may comprise at least one of silver (Ag), gold (Au) or copper (Cu). Further, the first and second wavelength ranges being separate from one another without mutual interference. In addition, the method may comprise steps of emitting a laser light onto the test structure inside the body of the animal so that one or more of the marker particles sprayed onto the test structure emit optical signals comprising the fluorescence signals and the Raman signals; collecting, by an optical fiber bundle of the medical imaging device, the optical signals emitted from the one or more of the marker particles sprayed onto the test structure; separating the optical signals into a first optical path containing the fluorescence signals in the first wavelength range and a second optical path containing the Raman signals in the second wavelength range; and simultaneously detecting the fluorescence signals in the first optical path for constructing a fluorescence image and the Raman signals in the second optical path for constructing a SERS (Surface Enhanced Raman Scattering) spectrum. In this method, the fluorescence image may be indicative of locations of the multiple targets in the test structure based on the detected fluorescence signals, and the SERS spectrum may be indicative of types of the multiple targets in the test structure based on the detected Raman signals.

Example 2

In the method of Example 1, the emitted optical signals further contain scattered laser light in the emitting step, and, before said separating step, the method further comprises a step of removing, by filtering, the scattered laser light from the emitted optical signals to form a filtered optical signal.

Example 3

In the method of Example 1, each of the marker particles further comprises a silica shell surrounding the one or more fluorescence dyes, the one or more Raman marker particles and the one or more metallic nanoparticles.

Example 4

In the method of Example 3, each of the marker particles further comprises a core particle which is surrounded by the one or more fluorescence dyes, the one or more Raman marker particles, the one or more metallic nanoparticles and the silica shell, and which is formed of at least one of silica and magnetic materials.

Example 5

In the method of Example 1, each of the marker particles further comprises a core particle and the one or more Raman marker particles and the one or more metallic nanoparticles are dispersed inside the core particle.

Example 6

In the method of Example 1, the animal comprises a human.

Example 7

In the method of Example 1, the fluorescence dye comprises n types of fluorescence dyes and the Raman marker particles comprises m types of Raman marker particles, the plurality of marker particles is capable of indicating m×n types of targets in the test structure, and m is an integer greater than or equal to 1 and n is an integer ranging from 2 to 4.

Example 8

According to another aspect of the present disclosure, there is provided a medical imaging device for simultaneously detecting fluorescence signals and Raman signals for a plurality of targets in a test structure inside a body of an animal. The medical imaging device may comprise a plurality of marker particles. In this device, each marker particle may be adapted to simultaneously generate fluorescence signals in a first wavelength range and Raman signals in a second wavelength range and include one or more Raman marker particles, one or more receptors, one or more fluorescence dyes and one or more metallic nanoparticles comprising at least one of silver (Ag), gold (Au) or copper (Cu). Further, the first and second wavelength ranges are separate from one another without mutual interference. In addition, the medical imaging device may comprise a spray device adapted to spray the plurality of marker particles onto the test structure; a probe including an optical fiber bundle configured to guide a laser light onto the test structure and collect optical signals comprising the fluorescence signals and the Raman signals emitted from one or more of the marker particles sprayed onto the test structure in response to the laser light; a scanner connected to the probe and adapted to scan the optical signals comprising the fluorescence signals and the Raman signals; a light separator comprising a beam splitter connected to the scanner to separate a path of the optical signals into a first path including the fluorescence signals in the first wavelength range and a second path including the Raman signals in the second wavelength range; a fluorescence signal detector configured to detect the fluorescence signals from in the first path for constructing a fluorescence image; and a Raman signal detector configured to detect the Raman signals in the second path for constructing a SERS spectrum. In this device, the fluorescence image may be indicative of locations of the multiple targets in the test structure based on the detected fluorescence signals, and the SERS spectrum may be indicative of types of the multiple targets in the test structure based on the detected Raman signals.

Example 9

In the device of Example 8, the light separator further comprises an edge filter placed between the scanner, the fluorescence signal detector and the Raman signal detector, to remove, by filtering, the laser light from the optical signals incoming from the scanner.

Example 10

In the device of Example 8, each of the marker particles further comprises a silica shell surrounding the one or more fluorescence dyes, the one or more Raman marker particles and the one or more metallic nanoparticles.

Example 11

In the device of Example 10, each of the marker particles further comprises a core particle which is surrounded by the one or more fluorescence dyes, the one or more Raman marker particles, the one or more metallic nanoparticles and the silica shell, and the core particle is formed of at least one of silica and magnetic materials.

Example 12

In the device of Example 8, each of the marker particles further comprises a core particle and the one or more Raman marker particles and the one or more metallic nanoparticles are dispersed inside the core particle.

Example 13

In the device of Example 8, the receptors comprise any one selected from the group consisting of enzymatic substrate, ligand, amino acid, peptide, protein, nucleic acid, lipid, co-factor, carbohydrate and antibody.

Example 14

In the device of Example 8, the fluorescence dye comprises n types of fluorescence dyes and the Raman marker particles comprises m types of Raman marker particles, the plurality of marker particles is capable of indicating m×n types of targets in the test structure, and m is an integer greater than or equal to 1 and n is an integer ranging from 2 to 4.

Example 15

According to another aspect of the present disclosure, there is provided a medical imaging device for simultaneously detecting fluorescence signals and Raman signals for a plurality of targets in a test structure inside a body of an animal. The medical imaging device may comprise a storage tank containing a plurality of marker particles. In this device, each marker particle may be adapted to simultaneously generate fluorescence signals in a first wavelength range and Raman signals in a second wavelength range. The first and second wavelength ranges, may be separate from one another without mutual interference. In addition, the medical imaging device may comprise a spray device adapted to spray the plurality of marker particles from the storage tank onto the test structure; a probe including an optical fiber bundle configured to guide a laser light onto the test structure and simultaneously collect optical signals comprising the fluorescence signals and the Raman signals emitted from one or more of the marker particles sprayed onto the test structure in response to the laser light, the optical fiber bundle comprising a plurality of optical fibers, each optical fiber configured to collect one of the optical signals indicative of a pixel among a plurality of pixels defining an image of the test structure; a scanner connected to the probe and adapted to confocally scan the collected optical signals received from the optical fiber bundle; a light separator connected to the scanner to separate a path of the scanned optical signals into a first path including the fluorescence signals in the first wavelength range and a second path including the Raman signals in the second wavelength range; a fluorescence signal detector configured to detect the fluorescence signals in the first path, while the detected fluorescence signals are indicative of pixels associated with the plurality of targets to which the sprayed marker particles are attached; a Raman signal detector configured to detect the Raman signals in the second path and construct a SERS spectrum indicative of at least one property of the plurality of targets in the test structure based on the detected Raman signals; and an image processor configured to construct the image of the test structure indicative of locations of the plurality of targets in the test structure based on at least the detected fluorescence signals in the scanned optical signals.

Example 16

In the device of Example 15, the at least one property of the plurality of targets is indicative of at least one of a type, an amount, or morphological characteristics.

Example 17

In the device of Example 15, each of the marker particles includes one or more Raman marker particles and one or more fluorescence dyes.

Example 18

In the device of Example 17, the plurality of marker particles includes m types of Raman marker particles and n types of fluorescence dyes, and the image is indicative of the locations of m×n targets in the test structure and the SERS spectrum is indicative of the at least one property of m×n targets in the test structure, and m is an integer greater than or equal to 1 and n is an integer ranging from 2 to 4.

Example 19

In the device of Example 17, each of the marker particles further comprises one or more metallic nanoparticles and a core particle, and the one or more Raman marker particles and the one or more metallic nanoparticles surround the core particle, each of the Raman marker particles being adhered to one of the metallic nanoparticles.

Example 20

In the device of Example 19, each of the marker particles further comprises one or more metallic nanoparticles and a core particle, and the one or more Raman marker particles and the one or more metallic nanoparticles are dispersed inside the core particle.

Example 21

According to another aspect of the present disclosure, there is provided a medical imaging device for simultaneously detecting fluorescence signals and Raman signals for a plurality of targets in a test structure inside a body of an animal. The medical imaging device may comprise a storage tank containing a plurality of marker particles. In this device, each marker particle may be adapted to simultaneously generate one or more fluorescence signals in a first wavelength range and one or more Raman signals in a second wavelength range. The first and second wavelength ranges may be separate from one another without mutual interference. In addition, the medical imaging device may comprise a spray device adapted to spray the plurality of marker particles from the storage tank onto the test structure; a first and a second light source configured to generate a first and a second laser light, respectively; a probe configured to guide the laser lights from the first and the second light sources onto the test structure and collect optical signals comprising the fluorescence signals and the Raman signals emitted from one or more of the marker particles sprayed onto the test structure in response to the laser lights; a light separator configured to separate a path of the optical signals from the probe into a first path including the fluorescence signals in the first wavelength range and a second path including the Raman signals in the second wavelength range; a fluorescence signal detector configured to detect the fluorescence signals in the first path for constructing a fluorescence image indicative of locations of the plurality of targets in the test structure based on the detected fluorescence signals; and a Raman signal detector configured to detect the Raman signals in the second path for constructing a SERS (Surface Enhanced Raman Scattering) spectrum indicative of at least one property of the plurality of targets in the test structure based on the detected Raman signals.

Example 22

In the device of Example 21, the first laser light has a first laser wavelength and the marker particles are adapted to emit the fluorescence signals in response to the first laser light.

Example 23

In the device of Example 21, the second laser light has a second laser wavelength and the marker particles are adapted to emit the Raman signals in response to the second laser light.

Example 24

In the device of Example 21, the first and the second laser lights have a first and a second laser wavelength, respectively, and the marker particles are adapted to emit the fluorescence signals and the Raman signals in response to the first and second laser lights, respectively.

Example 25

In the device of Example 21, the first laser wavelength is greater than the second wavelength.

Example 26

In the device of Example 21, the first laser wavelength is less than the second wavelength.

Example 27

In the device of Example 25, the first laser wavelength ranges between 600 nm and 800 nm and the second laser wavelength ranges between 400 nm and 600 nm.

Example 28

In the device of Example 26, the first laser wavelength ranges between 600 nm and 800 nm and the second laser wavelength ranges between 400 nm and 600 nm.

Example 29

In the device of Example 21, each of the marker particles includes one or more Raman marker particles and one or more fluorescence dyes.

Example 30

In the device of Example 29, each of the marker particles further comprises one or more metallic nanoparticles and a core particle, and the one or more Raman marker particles and the one or more metallic nanoparticles surround the core particle, each of the Raman marker particles being adhered to one of the metallic nanoparticles.

Example 31

In the device of Example 29, each of the marker particles further comprises one or more metallic nanoparticles and a core particle, and the one or more Raman marker particles and the one or more metallic nanoparticles are dispersed inside the core particle.

Example 32

In the device of Example 21, the at least one property of the plurality of targets is indicative of at least one of a type, an amount, or morphological characteristics.

What is claimed is:

1. A method for simultaneously detecting, by a medical imaging device, fluorescence signals and Raman signals for multiple targets in a test structure inside a body of an animal, the method comprising steps of:
   directly spraying a plurality of marker particles onto the test structure, each marker particle being adapted to simultaneously generate fluorescence signals in a first wavelength range and Raman signals in a second wavelength range and including one or more Raman marker particles, receptors, one or more fluorescence dyes and one or more metallic nanoparticles comprising at least one of silver (Ag), gold (Au) or copper (Cu), the first and second wavelength ranges being separate from one another without mutual interference;
   emitting a laser light onto the test structure inside the body of the animal so that one or more of the marker particles sprayed onto the test structure emit optical signals comprising the fluorescence signals and the Raman signals;
   collecting, by an optical fiber bundle of the medical imaging device, the optical signals emitted from the one or more of the marker particles sprayed onto the test structure;
   separating the optical signals into a first optical path containing the fluorescence signals in the first wavelength range and a second optical path containing the Raman signals in the second wavelength range; and
   simultaneously detecting the fluorescence signals in the first optical path for constructing a fluorescence image indicative of locations of the multiple targets in the test structure based on the detected fluorescence signals, and the Raman signals in the second optical path for constructing a SERS (Surface Enhanced Raman Scattering) spectrum indicative of types of the multiple targets in the test structure based on the detected Raman signals.

2. The method of claim 1, wherein in said emitting step, the emitted optical signals further contain scattered laser light, and before said separating step, further comprising a step of:
   removing, by filtering, the scattered laser light from the emitted optical signals to form a filtered optical signal.

3. The method of claim 1, wherein each of the marker particles further comprises a silica shell surrounding the one or more fluorescence dyes, the one or more Raman marker particles and the one or more metallic nanoparticles.

4. The method of claim 3, wherein each of the marker particles further comprises a core particle which is surrounded by the one or more fluorescence dyes, the one or more Raman marker particles, the one or more metallic nanoparticles and the silica shell, and which is formed of at least one of silica and magnetic materials.

5. The method of claim 1, wherein each of the marker particles further comprises a core particle and wherein the one or more Raman marker particles and the one or more metallic nanoparticles are dispersed inside the core particle.

6. The method of claim 1, wherein the animal comprises a human.

7. The method of claim 1, wherein the fluorescence dye comprises n types of fluorescence dyes and the Raman marker particles comprises m types of Raman marker particles, wherein the plurality of marker particles is capable of indicating m×n types of targets in the test structure, and wherein m is an integer greater than or equal to 1 and n is an integer ranging from 2 to 4.

8. A medical imaging device for simultaneously detecting fluorescence signals and Raman signals for a plurality of targets in a test structure inside a body of an animal, the medical imaging device comprising:
   a plurality of marker particles, each marker particle being adapted to simultaneously generate fluorescence signals in a first wavelength range and Raman signals in a second wavelength range and including one or more Raman marker particles, one or more receptors, one or more fluorescence dyes and one or more metallic nanoparticles comprising at least one of silver (Ag), gold (Au) or copper (Cu), wherein the first and second wavelength ranges are separate from one another without mutual interference;
   a spray device adapted to spray the plurality of marker particles onto the test structure;
   a probe including an optical fiber bundle configured to guide a laser light onto the test structure and collect optical signals comprising the fluorescence signals and the Raman signals emitted from one or more of the marker particles sprayed onto the test structure in response to the laser light;
   a scanner connected to the probe and adapted to scan the optical signals comprising the fluorescence signals and the Raman signals;
   a light separator comprising a beam splitter connected to the scanner to separate a path of the optical signals into a first path including the fluorescence signals in the first wavelength range and a second path including the Raman signals in the second wavelength range;
   a fluorescence signal detector configured to detect the fluorescence signals from the optical signals in the first path for constructing a fluorescence image indicative of locations of the plurality of targets in the test structure based on the detected fluorescence signals; and a Raman signal detector configured to detect the Raman signals from the optical signals in the second path for constructing a SERS (Surface Enhanced Raman Scattering) spectrum indicative of types of the plurality of targets in the test structure based on the detected Raman signals.

9. The medical imaging device of claim 8, wherein the light separator further comprises an edge filter placed between the scanner, the fluorescence signal detector and the Raman signal detector, to remove, by filtering, the laser light from the optical signals incoming from the scanner.

10. The medical imaging device of claim 8, wherein each of the marker particles further comprises a silica shell surrounding the one or more fluorescence dyes, the one or more Raman marker particles and the one or more metallic nanoparticles.

11. The medical imaging device of claim 10, wherein each of the marker particles further comprises a core particle which is surrounded by the one or more fluorescence dyes, the one or more Raman marker particles, the one or more metallic nanoparticles and the silica shell, and the core particle is formed of at least one of silica and magnetic materials.

12. The medical imaging device of claim 8, wherein each of the marker particles further comprises a core particle and wherein the one or more Raman marker particles and the one or more metallic nanoparticles are dispersed inside the core particle.

13. The medical imaging device of claim 8, wherein the receptors comprise any one selected from the group consisting of enzymatic substrate, ligand, amino acid, peptide, protein, nucleic acid, lipid, co-factor, carbohydrate and antibody.

14. The medical imaging device of claim 8, wherein the fluorescence dye comprises n types of fluorescence dyes and the Raman marker particles comprises m types of Raman marker particles, wherein the plurality of marker particles is capable of indicating m×n types of targets in the test structure, and wherein m is an integer greater than or equal to 1 and n is an integer ranging from 2 to 4.

* * * * *